US009603507B2

(12) United States Patent
Umemoto et al.

(10) Patent No.: US 9,603,507 B2
(45) Date of Patent: Mar. 28, 2017

(54) INSERTION DEVICE

(71) Applicant: OLYMPUS CORPORATION, Tokyo (JP)

(72) Inventors: Yoshitaka Umemoto, Hachioji (JP); Kimihiko Naito, Kawasaki (JP); Hiroaki Miyoshi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 300 days.

(21) Appl. No.: 14/154,288

(22) Filed: Jan. 14, 2014

(65) Prior Publication Data

US 2014/0194682 A1    Jul. 10, 2014

Related U.S. Application Data

(63) Continuation of application No. PCT/JP2013/067541, filed on Jun. 26, 2013.

(30) Foreign Application Priority Data

Jun. 27, 2012  (JP) ................................ 2012-144542

(51) Int. Cl.
*A61B 1/00* (2006.01)
*A61B 1/04* (2006.01)
*A61B 1/05* (2006.01)

(52) U.S. Cl.
CPC .............. *A61B 1/0016* (2013.01); *A61B 1/00* (2013.01); *A61B 1/00009* (2013.01);
(Continued)

(58) Field of Classification Search
CPC ............ A61B 1/00133; A61B 1/00135; A61B 1/00154; A61B 1/00156; A61B 1/0008;
(Continued)

(56) References Cited

U.S. PATENT DOCUMENTS

| 2008/0009675 A1* | 1/2008 | Kura ................... A61B 1/00147 600/137 |
| 2010/0113876 A1* | 5/2010 | Ishihara ............. A61B 1/00147 600/117 |

(Continued)

FOREIGN PATENT DOCUMENTS

| JP | 2005-323888 A | 11/2005 |
| JP | 2006-149581 A | 6/2006 |

(Continued)

OTHER PUBLICATIONS

English translation of International Preliminary Report on Patentability together with the Written Opinion dated Jan. 8, 2015 received in related International Application No. PCT/JP2013/067541.

(Continued)

*Primary Examiner* — Timothy J Neal
(74) *Attorney, Agent, or Firm* — Scully, Scott, Murphy & Presser, PC

(57) ABSTRACT

An insertion device includes an idle state detector detecting an idle state in which an insertion section does not move in directions along the longitudinal axis when a rotation unit rotates in directions around the longitudinal axis, and a movement displacement calculator calculating a rotation direction and amount of the rotation unit based on a driving direction and amount of the driving member and calculating a movement displacement of the insertion section from a reference position in directions parallel to the longitudinal axis based on the rotation direction and amount of the rotation unit. The movement displacement calculator calculates the movement displacement of the insertion section so that a movement amount of the insertion section in the longitudinal directions while the idle state being detected is zero.

12 Claims, 14 Drawing Sheets

(52) U.S. Cl.
CPC ...... *A61B 1/00055* (2013.01); *A61B 1/00154* (2013.01); *A61B 1/04* (2013.01); *A61B 1/0002* (2013.01); *A61B 1/05* (2013.01)

(58) Field of Classification Search
CPC . A61B 1/0016; A61B 1/00055; A61B 1/0002; A61B 1/04; A61B 1/00009
USPC ................ 600/103, 104, 117, 118, 127, 137; 604/95.01
See application file for complete search history.

(56) References Cited

U.S. PATENT DOCUMENTS

2011/0242301 A1    10/2011  Morita
2012/0029281 A1*  2/2012  Frassica ............. A61B 1/00082
                                                             600/114

FOREIGN PATENT DOCUMENTS

| JP | 2006-230620 A | 9/2006 |
| JP | 2007-185394 A | 7/2007 |
| JP | 2008-220672 A | 9/2008 |
| JP | 2011-206251 A | 10/2011 |

OTHER PUBLICATIONS

International Search Report dated Aug. 20, 2013 issued in PCT/JP2013/067541.

* cited by examiner

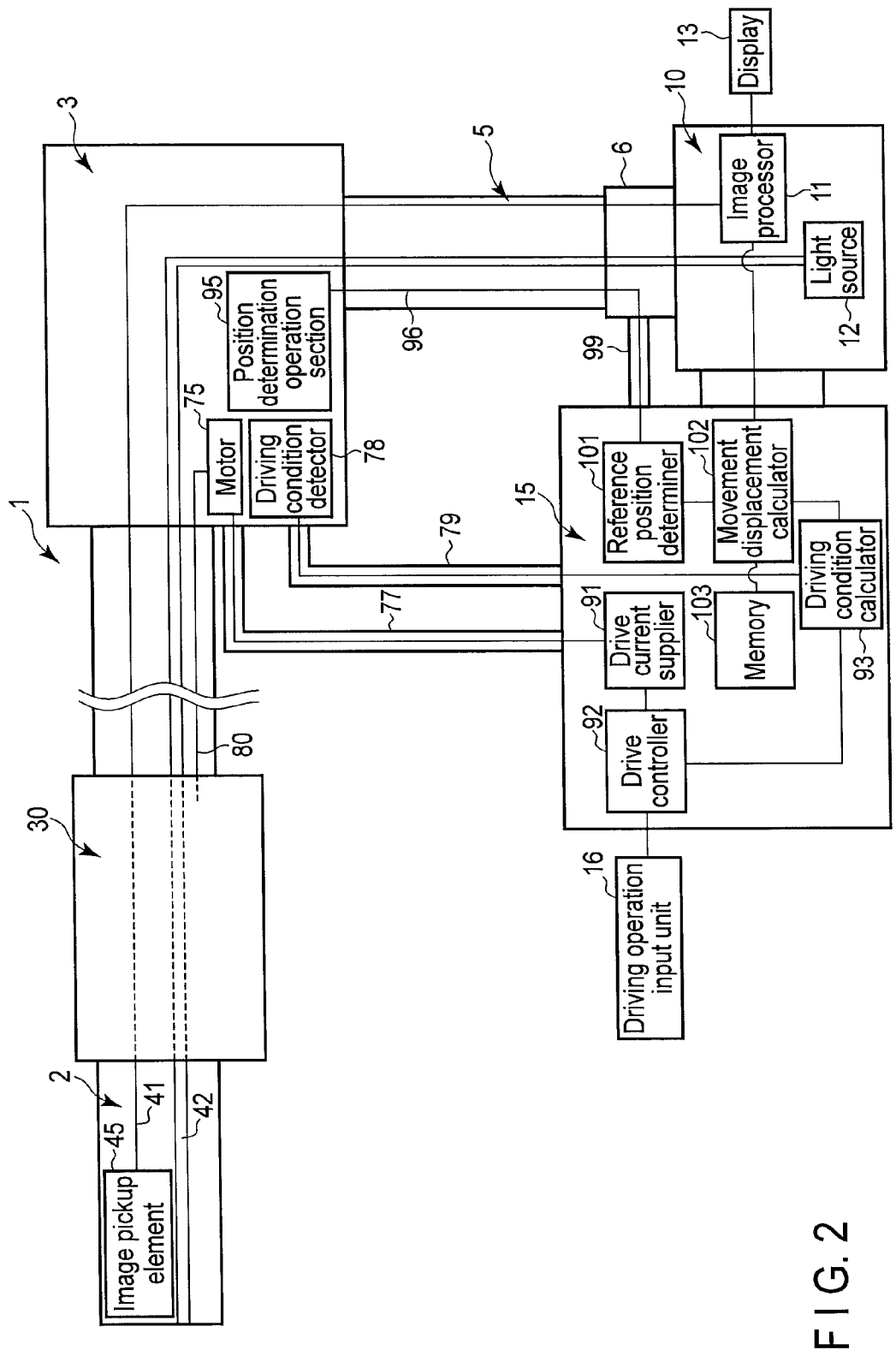
F I G. 2

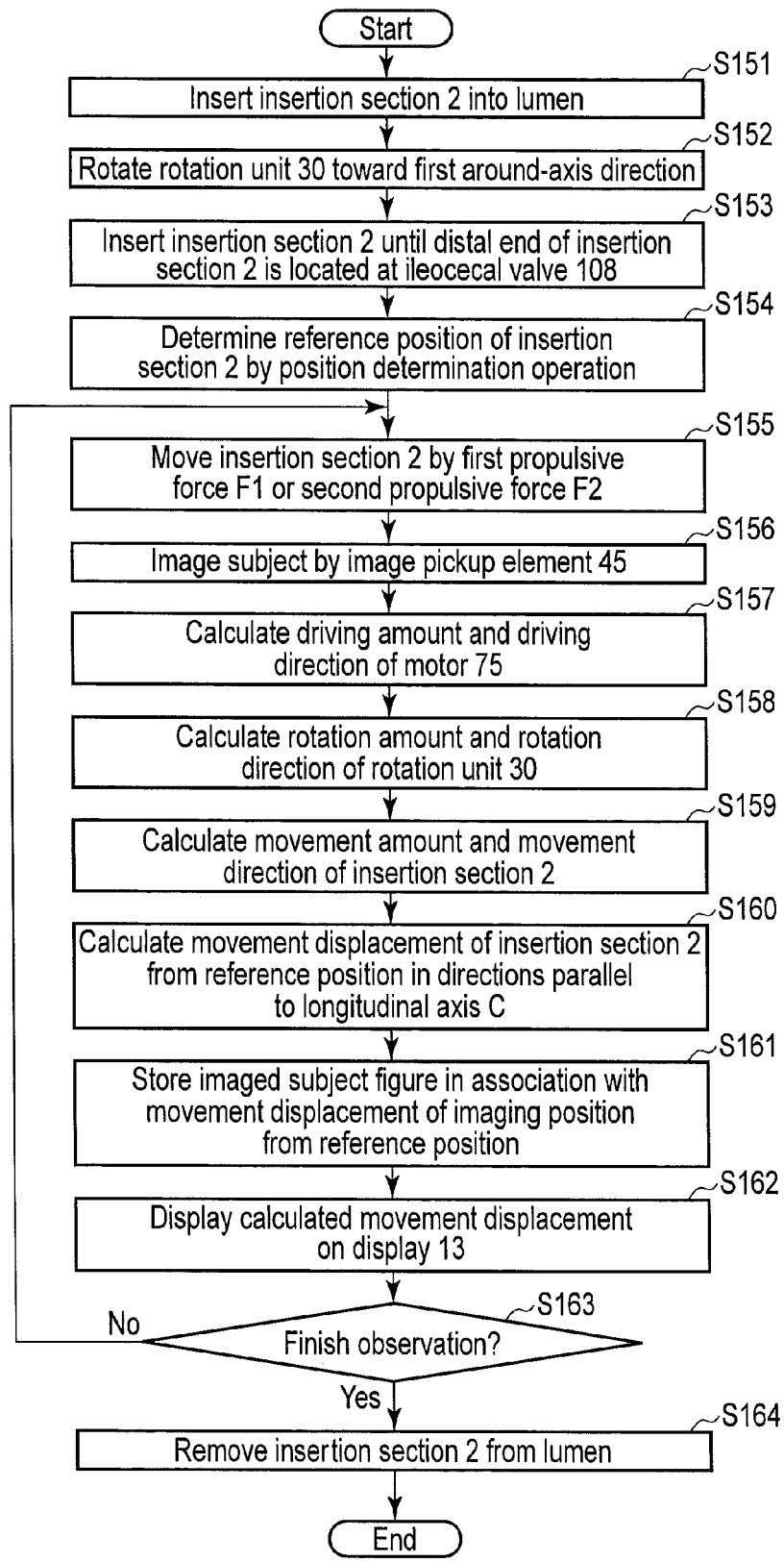
F I G. 7

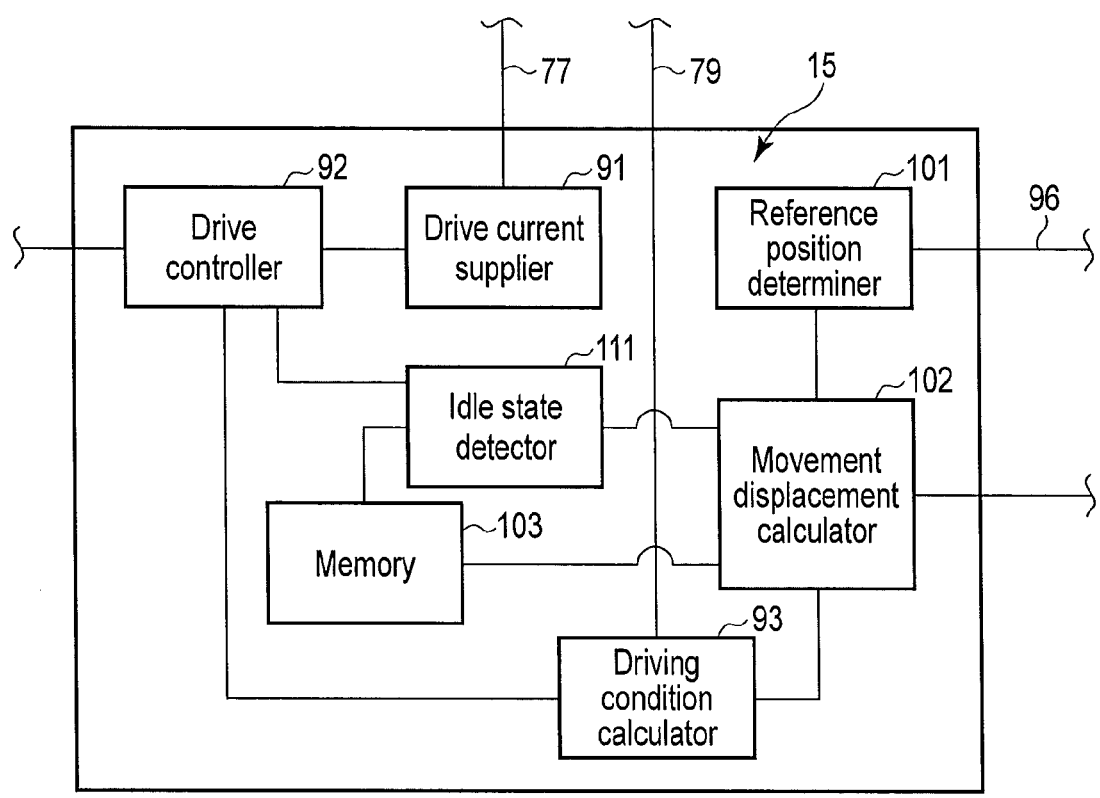
F I G. 10

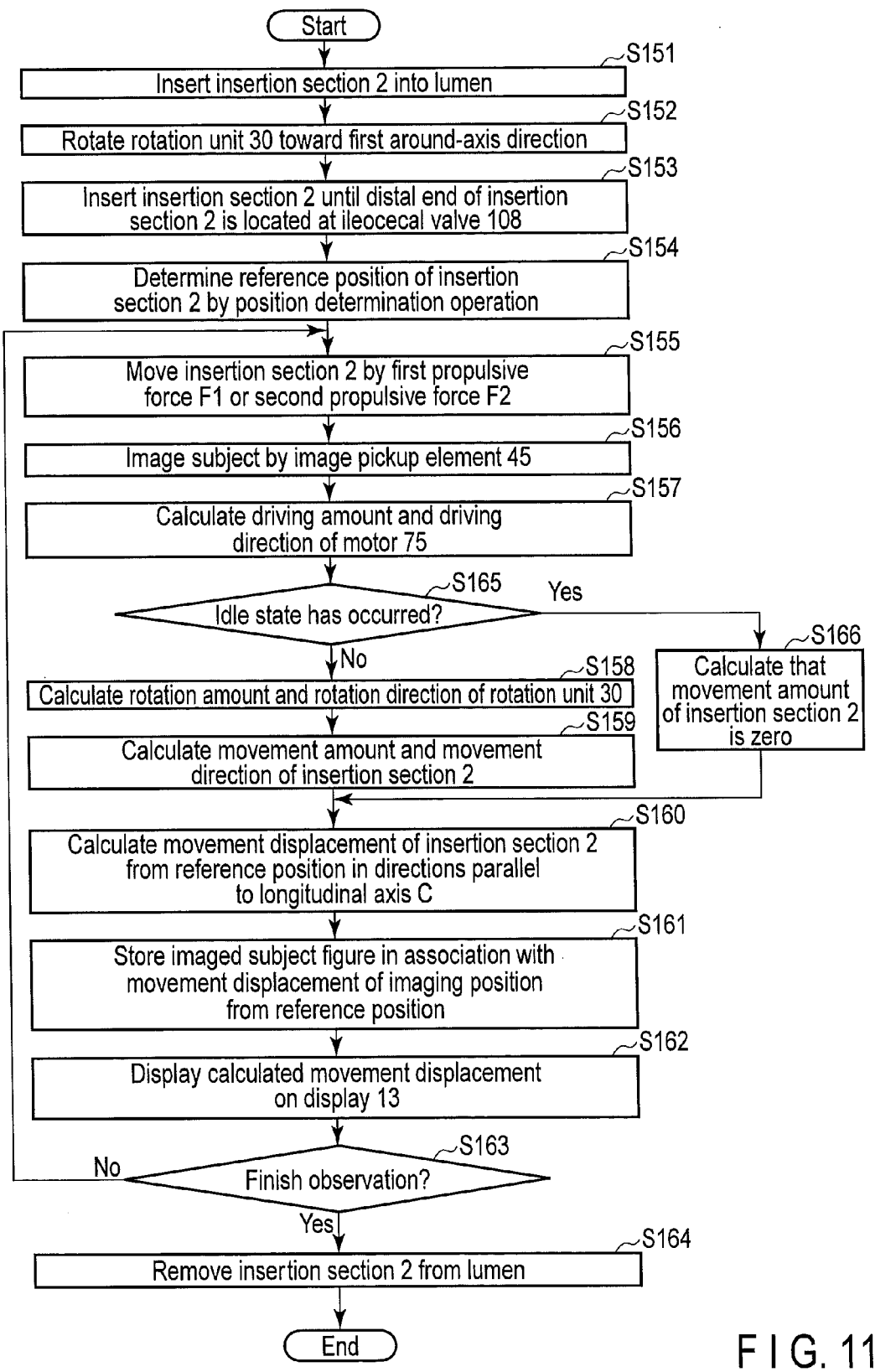
F I G. 11

INSERTION DEVICE

CROSS-REFERENCE TO RELATED APPLICATIONS

This is a Continuation application of PCT Application No. PCT/JP2013/067541, filed Jun. 26, 2013 and based upon and claiming the benefit of priority from prior Japanese Patent Application No. 2012-144542, filed Jun. 27, 2012, the entire contents of which are incorporated herein by reference.

BACKGROUND OF THE INVENTION

1. Field of the Invention

The present invention relates to an insertion device comprising an insertion section extending along a longitudinal axis, and a rotation unit rotatable relative to the insertion section in directions around the longitudinal axis.

2. Description of the Related Art

Jpn. Pat. Appln. KOKAI Publication No. 2008-220672 has disclosed an endoscope device which is an insertion device including an insertion section extending from a proximal direction toward a distal direction along a longitudinal axis. In this endoscope device, a motor which is a driving member is driven, and the insertion section thereby moves along the longitudinal axis. The driving direction and driving amount of the motor are detected by an encoder. An insertion length calculator then calculates a dimension along the longitudinal axis between the motor and the distal end of the insertion section in accordance with the detected driving direction and driving amount of the motor. As a result, a dimension of the part of the insertion section inserted into a lumen along the longitudinal axis is calculated. In this endoscope device, an image of a subject is generated by an image capture. The dimension of the part inserted into the lumen along the longitudinal axis and the image of the subject are stored in a memory in association with each other.

Jpn. Pat. Appln. KOKAI Publication No. 2005-323888 has disclosed an endoscope device which is an insertion device including an insertion section extending along a longitudinal axis, and a rotation unit rotatable relative to the insertion section in directions around the longitudinal axis. The rotation unit includes a spiral fin portion spirally extending about the longitudinal axis. A position in the spiral fin portion is toward a first around-axis direction which is one of directions around the longitudinal axis as the position in the spiral fin portion is from a proximal direction toward a distal direction. In a lumen, the rotation unit is rotated in the first around-axis direction while the spiral fin portion is in contact with a luminal wall, so that a first propulsive force is applied to the insertion section and the rotation unit toward the distal direction. On the other hand, the rotation unit is rotated in a second around-axis direction opposite to the first around-axis direction while the spiral fin portion is in contact with the luminal wall, so that a second propulsive force is applied to the insertion section and the rotation unit toward the proximal direction. The first propulsive force and the second propulsive force ensure the mobility of the insertion section in directions parallel to the longitudinal axis even in a lumen such as a small intestine having many bent parts.

BRIEF SUMMARY OF THE INVENTION

According to one aspect of the invention, an insertion device includes that: an insertion section extending from a proximal direction toward a distal direction along a longitudinal axis; a rotation unit provided to an outer peripheral direction side of the insertion section rotatably relative to the insertion section in directions around the longitudinal axis, the rotation unit including a spiral fin portion spirally extending about the longitudinal axis; a driving member which is configured to be driven to generate a driving force of rotating the rotation unit; a driving force transmission unit which is configured to transmit the driving force generated in the driving member to the rotation unit; a reference position determiner which is configured to determine a reference position that is a position of the insertion section serving as a reference; an idle state detector which is configured to detect an idle state in which the insertion section does not move in directions along the longitudinal axis even when the rotation unit rotates in one of the directions around the longitudinal axis; and a movement displacement calculator which is configured to calculate a rotation direction and a rotation amount of the rotation unit in accordance with a driving direction and a driving amount of the driving member, and configured to calculate a movement displacement of the insertion section from the reference position in directions parallel to the longitudinal axis in accordance with the rotation direction and the rotation amount of the rotation unit, the movement displacement calculator being configured to calculate the movement displacement of the insertion section from the reference position so that a movement amount of the insertion section in the directions parallel to the longitudinal axis while the idle state being detected by the idle state detector is zero.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic block diagram showing the endoscope device according to the first embodiment;

FIG. 7 is a flowchart showing one method of observing the small intestine by the endoscope device according to the first embodiment;

FIG. 10 is a schematic block diagram showing the configuration of a control unit of an endoscope device according to a second embodiment;

FIG. 11 is a flowchart showing a method of observing a small intestine by the endoscope device according to the second embodiment;

DETAILED DESCRIPTION OF THE INVENTION

First Embodiment

Figure 1:
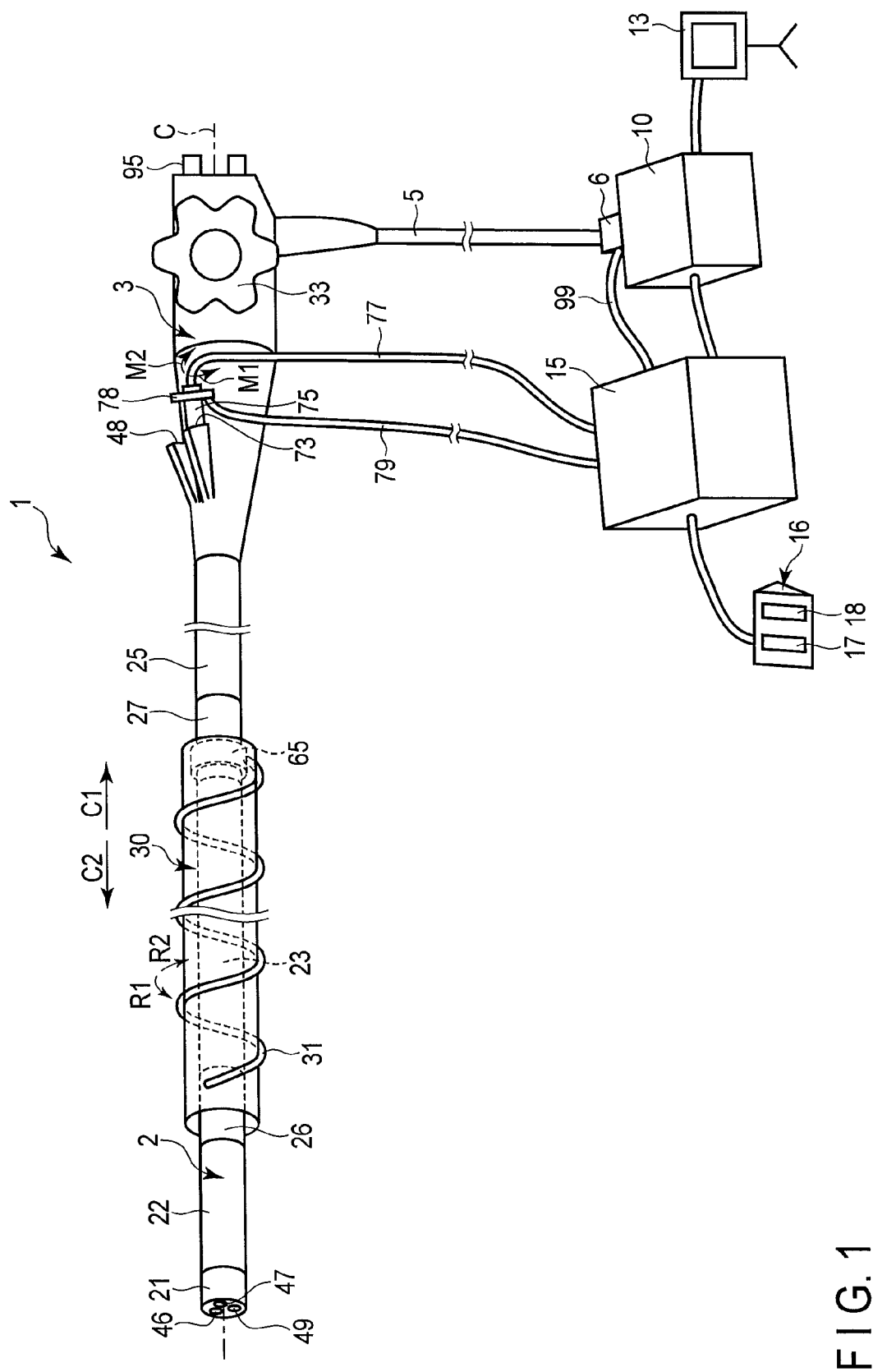
FIG. 1 is a schematic diagram showing an endoscope device according to a first embodiment.

A first embodiment of the present invention is described with reference to FIG. 1 to FIG. 9C. FIG. 1 and FIG. 2 are diagrams showing an endoscope device 1 which is an insertion device according to a first embodiment. As shown in FIG. 1, the endoscope device 1 has a longitudinal axis C. One of directions parallel to the longitudinal axis C is a proximal direction (direction of an arrow C1 in FIG. 1), and the direction opposite to the proximal direction is a distal direction (direction of an arrow C2 in FIG. 1). As shown in FIG. 1 and FIG. 2, the endoscope device 1 includes an insertion section (endoscope insertion section) 2 extending from a proximal direction toward a distal direction along the longitudinal axis C, and an operation section (endoscope operation section) 3 provided to the proximal direction side of the insertion section 2. The insertion section 2 is configured to be inserted into a body cavity when the endoscope device 1 is used.

One end of a universal cable 5 is connected to the operation section 3. The other end of the universal cable 5 is connected to an observation processing unit 10 via a connector 6. The observation processing unit 10 includes an image processor 11 and a light source 12. The observation processing unit 10 is electrically connected to a display 13 such as a monitor. The observation processing unit 10 is also electrically connected to a control unit 15. The control unit 15 is electrically connected to a driving operation input unit 16 such as a foot switch. The driving operation input unit 16 includes a first operation input section 17 and a second operation input section 18.

The insertion section 2 includes a distal hard section 21 provided to the most distal-direction side part, a bending section 22 provided to the proximal direction side of the distal hard section 21, a first flexible section 23 provided to the proximal direction side of the bending section 22, and a second flexible section 25 provided to the proximal direction side of the first flexible section 23. The bending section 22 and the first flexible section 23 are connected to each other by a first intermediary connection section 26. The first flexible section 23 and the second flexible section 25 are connected to each other by a second intermediary connection section 27.

A rotation unit 30 is provided to an outer peripheral direction side of the insertion section 2. The insertion section 2 is inserted through the rotation unit 30. The rotation unit 30 extends along the longitudinal axis C between the first intermediary connection section 26 and the second intermediary connection section 27. The rotation unit 30 is rotatable relative to the insertion section 2 in directions around the longitudinal axis. Here, one of directions around the longitudinal axis is a first around-axis direction (direction of an arrow R1 in FIG. 1), and the direction opposite to the first around-axis direction is a second around-axis direction (direction of an arrow C2 in FIG. 1). In the present embodiment, a clockwise direction viewed from the proximal direction is the first around-axis direction, and a counterclockwise direction viewed from the proximal direction is the second around-axis direction. The rotation unit 30 includes a spiral fin portion 31 spirally extending about the longitudinal axis C. A position in the spiral fin portion 31 is toward the first around-axis direction as the position in the spiral fin portion is from the proximal direction to the distal direction.

Figure 3:
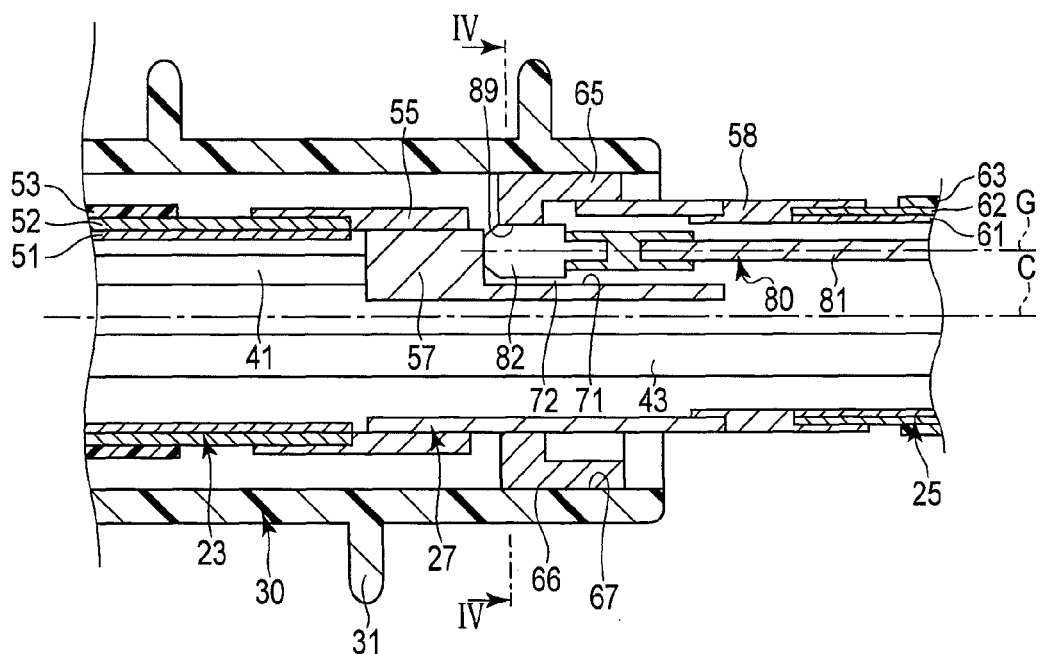
FIG. 3 is a schematic sectional view showing the configuration of a second intermediary connection section of an insertion section according to the first embodiment.
Figure 4:
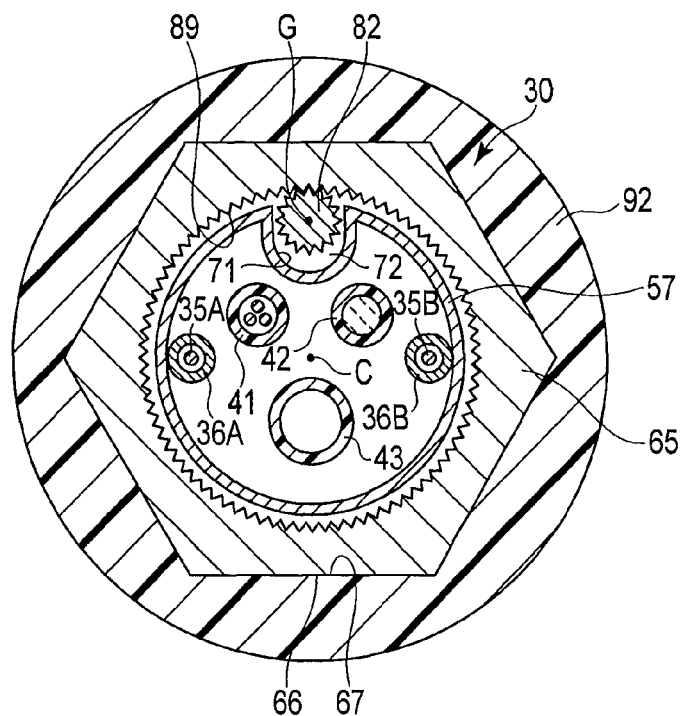
FIG. 4 is a sectional view taken along the line IV-IV of FIG. 3.

FIG. 3 is a diagram showing the configuration of the second intermediary connection section 27. FIG. 4 is a sectional view taken along the line IV-IV of FIG. 3. As shown in FIG. 1, a bending operation knob 33, which is a bending operation input section configured to input a bending operation of the bending section 22, is provided on the outer surface of the operation section 3. As shown in FIG. 4, bending wires 35A and 35B extend through an inside of the insertion section 2 along the longitudinal axis C. The proximal ends of the bending wires 35A and 35B are connected to pulleys (not shown) coupled to the bending operation knob 33 inside the operation section 3. The distal ends of the bending wires 35A and 35B are connected to a distal portion of the bending section 22. In response to the bending operation of the bending operation knob 33, the bending wire 35A or the bending wire 35B is pulled, and the bending section 22 bends.

Each of the bending wires 35A and 35B is inserted through a corresponding coil 36A or 36B. The proximal ends of the coils 36A and 36B are fixed to the inner peripheral portion of the operation section 3. The distal ends of the coils 36A and 36B are connected to the inner peripheral portion of the first intermediary connection section 26. In the present embodiment, the two bending wires 35A and 35B are provided, and the bending section 22 is bendable in two directions. However, for example, four bending wires may be provided, and the bending section 22 may be bendable in four directions. No bending section 22 may be provided.

As shown in FIG. 3 and FIG. 4, an imaging cable 41, a light guide 42, and a treatment tool channel tube 43 extend through the inside of the insertion section 2 along the longitudinal axis C. An image pickup element 45 configured to image a subject is provided inside the distal hard section 21 (the distal portion of the insertion section 2) (see FIG. 2). The image pickup element 45 is configured to image the subject through an observation window 46. The distal end of the imaging cable 41 is connected to the image pickup element 45. The imaging cable 41 extends through the inside of the insertion section 2, an inside of the operation section 3, and an inside of the universal cable 5, and has its proximal end connected to the image processor 11 of the observation processing unit 10. A subject figure obtained is processed by the image processor 11, and an image of the subject is generated. The generated image of the subject is displayed on the display 13.

The light guide 42 extends through the inside of the insertion section 2, the inside of the operation section 3, and the inside of the universal cable 5, and has its proximal end connected to the light source 12 of the observation processing unit 10. Light emitted from the light source 12 is guided by the light guide 42, and applied to the subject from an illumination window 47 in the distal portion (distal hard section 21) of the insertion section 2.

As shown in FIG. 1, a treatment tool insertion portion 48 into which a treatment tool such as a forceps is inserted is provided to the outer surface of the operation section 3. The treatment tool channel tube 43 has its proximal end connected to the treatment tool insertion portion 48, and extends through the inside of the insertion section 2 and the inside of the operation section 3. The treatment tool inserted from the treatment tool insertion portion 48 projects toward a distal direction from an opening 49 of the distal hard section 21 through the treatment tool channel tube 43. A treatment is then conducted by the treatment tool projecting from the opening 49 of the distal hard section 21.

As shown in FIG. 3, a metallic first helical tube (first flex) 51 is provided to the first flexible section 23. To the outer circumferential direction side of the first spiral tube 51 is covered with a metallic first flexible mesh tube (first flexible braid) 52. To the outer peripheral direction side of the first flexible mesh tube 52 is covered with a resin first flexible envelope 53. The proximal portion of the first helical tube 51 and the proximal portion of the first flexible reticular tube 52 are fitted in the distal portion of an intermediary member 55. The second intermediary connection section 27 includes a metallic base member 57. The proximal portion of the intermediary member 55 is fitted in the base member 57. In this way, the first flexible section 23 is coupled to the second intermediary connection section 27.

A metallic second helical tube (second flex) 61 is provided to the second flexible section 25. To the outer circumferential direction side of the second helical tube 61 is covered with a metallic second flexible mesh tube (second flexible braid) 62. To the outer peripheral direction side of the second flexible mesh tube 62 is covered with a resin second flexible tube envelope 63. The distal portion of the second helical tube 61 and the distal portion of the second flexible reticular tube 62 are fitted in an intermediary member 58. The intermediary member 58 is fitted in the base member 57. In this way, the second flexible section 25 is coupled to the second intermediary connection section 27.

A rotating tubular member 65 is attached to the second intermediary connection section 27 of the insertion section 2 so that the insertion section 2 is inserted therethrough. The rotating tubular member 65 is rotatable relative to the insertion section 2 in the directions around the longitudinal axis. The rotation unit 30 is located to the outer peripheral direction side of the rotating tubular member 65.

As shown in FIG. 4, the rotating tubular member 65 is provided with a polygonal outer peripheral portion 66 having a substantially hexagonal sectional shape in a section perpendicular to the longitudinal axis C. The rotation unit 30 is provided with a polygonal inner peripheral portion 67 in which a sectional shape in a section perpendicular to the longitudinal axis C passing through the rotating tubular member 65 is formed into a substantially hexagonal shape corresponding to the polygonal outer peripheral portion 66 of the rotating tubular member 65. Thus, the polygonal inner peripheral portion 67 of the rotation unit 30 is in close contact with the polygonal outer peripheral portion 66 of the rotating tubular member 65, and the rotation unit 30 is fixed to the outer circumferential direction side of the rotating tubular member 65. As a result, the rotation unit 30 is rotatable relative to the insertion section 2 in the directions around the longitudinal axis together with the rotating tubular member 65. That is, the base member 57 serves as a base portion to which the rotation unit 30 is attached via the rotating tubular member 65 rotatably in the directions around the longitudinal axis.

As shown in FIG. 2 and FIG. 3, a gear placement cavity 72 is defined by a cavity defining portion 71 in the base member 57 (base portion). The outside and the inside of the insertion section 2 are in communication with each other via the gear placement cavity 72.

As shown in FIG. 1, a member insertion portion 73 is provided to the outer surface of the operation section 3. A motor 75 which is a driving member is attached to the member insertion portion 73. One end of a motor cable 77 is connected to the motor 75. The control unit 15 includes a drive current supplier 91 and a drive controller 92. The other end of the motor cable 77 is connected to the drive current supplier 91. The drive current supplier 91 is electrically connected to the drive controller 92. A drive current is supplied to the motor 75 by the drive current supplier 91 via the motor cable 77. The drive current supplied from the drive current supplier 91 is adjusted by the drive controller 92. Thus, the driving amount and driving direction (driving condition) of the motor 75 are controlled. The motor 75 is rotationally drivable in a first driving direction (direction of an arrow M1 in FIG. 1) and a second driving direction (direction of an arrow M2 in FIG. 1). When the motor 75 is driven, a driving force to rotate the rotation unit 30 in one of the directions around the longitudinal axis is generated.

A driving condition detector 78 such as an encoder is attached to the motor 75. The driving condition of the motor 75 is detected by the driving condition detector 78. One end of a signal cable 79 is connected to the driving condition detector 78. The control unit 15 also includes a driving condition calculator 93. The other end of the signal cable 79 is connected to the driving condition calculator 93. The driving condition calculator 93 is configured to calculate the driving amount and the driving direction (driving condition) of the motor 75 in accordance with the detection result in the driving condition detector 78. The driving condition calculator 93 is electrically connected to the drive controller 92. The calculated driving condition of the motor 75 is fed back to the drive controller 92.

A driving force generated in the motor 75 is transmitted to the rotation unit 30 by a driving force transmission unit 80. As shown in FIG. 3 and FIG. 4, the driving force transmission unit 80 is provided in the second flexible section 25 and the gear placement cavity 72 of the insertion section 2. The driving force transmission unit 80 is rotatable around a driving axis G. The driving force transmission unit 80 includes a driving shaft 81 which is a linear member extending along the driving axis G, and a driving gear 82 provided to the distal direction side of the driving shaft 81. The driving shaft 81 is coupled to the driving gear 82 via a connection member 85. A proximal end of the driving shaft 81 is connected to the motor 75. When the motor 75 is driven, the driving shaft 81 and the driving gear 82 rotate in one of directions around the driving axis.

An inner peripheral gear portion 89 which is toothed with the driving gear 82 is provided on the inner peripheral portion of the rotating tubular member 65. The inner peripheral gear portion 89 is provided over all-round of the rotating tubular member 65 in the directions around the longitudinal axis. Thus, when the driving gear 82 rotates around the driving axis G, the rotating tubular member 65 rotates in one of the directions around the longitudinal axis. In response to the rotation of the rotating tubular member 65, the rotation unit 30 rotates relative to the insertion section 2 in one of the directions around the longitudinal axis. In this way, when the motor 75 is driven, the driving force to rotate the rotating tubular member 65 and the rotation unit 30 is transmitted by the driving force transmission unit 80.

Here, the motor 75 is rotationally driven toward the first driving direction (direction of the arrow M1 in FIG. 1) in response to the input of a driving operation in the first operation input section 17. Thus, the rotation unit 30 rotates relative to the insertion section 2 toward the first around-axis direction (direction of an arrow R1 in FIG. 1). On the other hand, the motor 75 is rotationally driven toward the second driving direction (direction of the arrow M2 in FIG. 1) in response to the input of the driving operation in the second operation input section 18. Thus, the rotation unit 30 rotates relative to the insertion section 2 toward the second around-axis direction (direction of an arrow R2 in FIG. 1).

As shown in FIG. 1 and FIG. 2, a button-shaped position determination operation section 95 is provided on the outer surface of the operation section 3. When the position determination operation section 95 is pressed, a position determination operation to determine a reference position of the insertion section 2 is input. One end of an electric signal line 96 is connected to the position determination operation section 95. One end of an intermediary cable 99 is connected to the universal cable 5 via the connector 6. The other end of the intermediary cable 99 is connected to the control unit 15.

The control unit 15 includes a reference position determiner 101. The other end of the electric signal line 96 is connected to the reference position determiner 101 through the inside of the universal cable 5 and through an inside of the intermediary cable 99. When the position determination operation is input in the position determination operation section 95, an operation signal is transmitted to the reference position determiner 101 via the electric signal line 96. The reference position determiner 101 is configured to determine, as the reference position of the insertion section 2, the position of the insertion section 2 when the operation signal is transmitted.

The control unit 20 includes a movement displacement calculator 102 and a memory 103. The movement displacement calculator 102 is electrically connected to the driving condition calculator 93, the reference position determiner 101, and the image processor 11 of the observation processing unit 10. The memory 103 is electrically connected to the movement displacement calculator 102. The processing in the movement displacement calculator 102 and the storage 103 will be described later.

Now, the function of the endoscope device 1 according to the present embodiment is described. When the endoscope device 1 is used, the insertion section 2 to which the rotating tubular member 65 and the rotation unit 30 are attached is inserted into a lumen. The motor 75 is then driven by the operation in the driving operation input unit 16. As a result, the driving force transmission unit 80 is rotated around the driving axis G, and a driving force is transmitted to the rotating tubular member 65 and the rotation unit 30. Thus, the rotating tubular member 65 and the rotation unit 30 rotate together relative to the insertion section 2 in one of the directions around the longitudinal axis.

Here, first rotation amount data I1 indicating the relation between the driving amount of the motor 75 which is the driving member toward the first driving direction and the rotation amount of the rotation unit 30 toward the first around-axis direction is stored in the memory 103. Second rotation amount data I2 indicating the relation between the driving amount of the motor 75 toward the second driving direction and the rotation amount of the rotation unit 30 toward the second around-axis direction is also stored in the storage 103. The first rotation amount data I1 and the second rotation amount data I2 are determined by, for example, the driving characteristics of the motor 75, and a gear ratio between the driving gear 82 and the inner peripheral gear portion 89.

Figure 5:
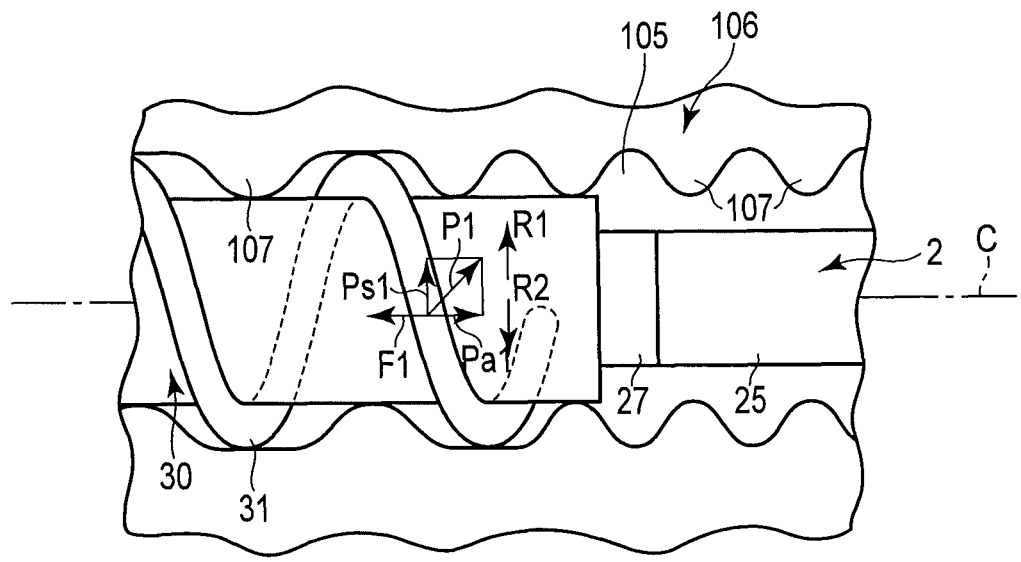
FIG. 5 is a schematic diagram showing a state in which a rotation unit according to the first embodiment rotates in a small intestine toward a first around-axis direction.

FIG. 5 is a diagram illustrating a state in which the rotation unit 30 rotates in a small intestine (lumen) 105 toward the first around-axis direction (direction of the arrow R1 in FIG. 5). As shown in FIG. 5, in the small intestine 105, the spiral fin portion 31 of the rotation unit 30 is all-roundly in contact with a wall of lumen 106 in the directions around the longitudinal axis. Thus, the rotation unit 30 is in an all-roundly pressed condition in which a press force is applied all-roundly in the directions around the longitudinal axis to the spiral fin portion 31 from the wall of lumen 106 toward the inner peripheral direction of the insertion section 2. When the rotation unit 30 is rotated toward the first around-axis direction in the all-roundly pressed condition, press force P1 is applied to the wall 106 of lumen from the spiral fin portion 31. The press force P1 is applied toward a direction inclined from the first around-axis direction to the proximal direction and perpendicular to the extending direction of the spiral fin portion 31. The press force P1 is divided into a circumferential force component Ps1 toward the first around-axis direction, and an axial force component Pa1 toward the proximal direction. First propulsive force F1 toward the distal direction is applied to the insertion section 2 and the rotation unit 30 from the wall of lumen 106 as a reaction to the axial force component Pa1 of the press force P1. The first propulsive force F1 ensures the insatiability of the insertion section 2 even in a lumen such as the small intestine 105 having many bent parts. That is, the mobility of the insertion section 2 toward the distal direction parallel to the longitudinal axis C is ensured in the small intestine 105.

The axial force component Pa1 of the press force P1 is applied to the wall 106 of lumen as a reaction force to the first propulsive force F1. Thus, when the insertion section 2 and the rotation unit 30 move toward the distal direction by the first propulsive force F1, the wall 106 of lumen moves toward the proximal direction by the axial force component Pa1 of the press force P1. Thus, folds 107 of the wall 106 of lumen come close together in a region to the proximal direction side of the spiral fin portion 31.

Figure 6:
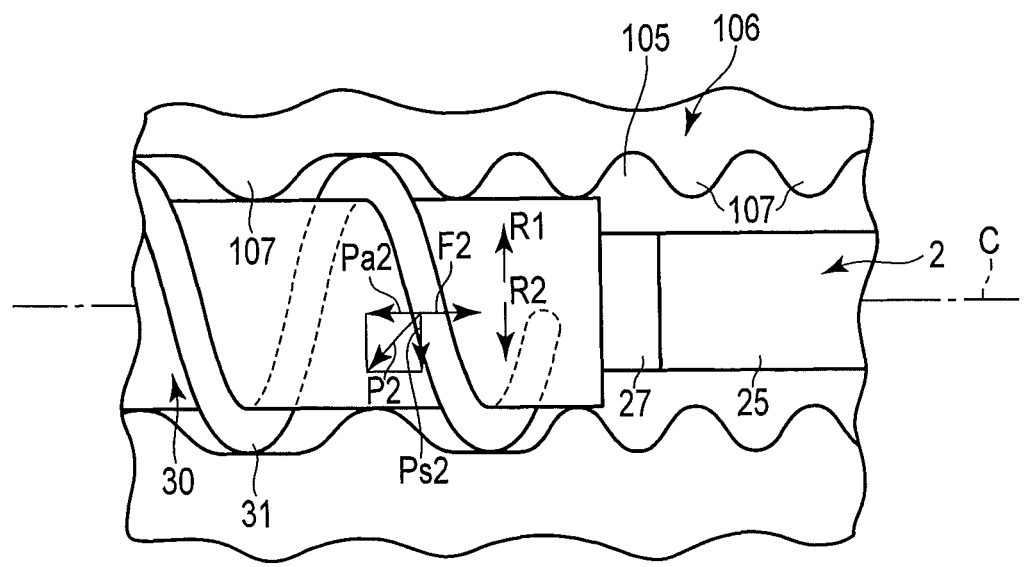
FIG. 6 is a schematic diagram showing a state in which the rotation unit according to the first embodiment rotates in the small intestine toward a second around-axis direction.

FIG. 6 is a diagram illustrating a state in which the rotation unit 30 rotates toward the second around-axis direction (direction of an arrow R2 in FIG. 6) in the small intestine (lumen) 105. As shown in FIG. 6, when the rotation unit 30 is rotated toward the second around-axis direction in the all-roundly pressed condition, press force P2 is applied to the wall 106 of lumen from the spiral fin portion 31. The press force P2 is applied toward a direction inclined from the second around-axis direction to the proximal direction and perpendicular to the extending direction of the spiral fin portion 31. The press force P2 is divided into a circumferential force component Ps2 toward the second around-axis direction, and an axial force component Pa2 toward the distal direction. Second propulsive force F2 toward the proximal direction is applied to the insertion section 2 and the rotation unit 30 from the wall 106 of lumen as a reaction to the axial force component Pa2 of the press force P2. The second propulsive force F2 also ensures the removability of the insertion section 2 even in a lumen such as the small intestine 105 having many bent parts. That is, the mobility of the insertion section 2 toward the proximal direction parallel to the longitudinal axis C is ensured in the small intestine 105.

The axial force component Pa2 of the press force P2 is applied to the wall 106 of lumen as a reaction force to the second propulsive force F2. Thus, when the insertion section 2 and the rotation unit 30 move toward the proximal direction by the second propulsive force F2, the wall 106 of lumen moves toward the distal direction by the axial force component Pa2 of the press force P2. Thus, the folds 107 which have been close together in the part to the proximal direction side of the spiral fin portion 31 are released from the close state.

Here, first movement amount data J1 indicating the relation between the rotation amount of the rotation unit 30 toward the first around-axis direction and the amount of the movement of the insertion section 2 relative to the wall 106 of lumen toward the distal direction is stored in the memory 103. Second movement amount data J2 indicating the relation between the rotation amount of the rotation unit 30 toward the second around-axis direction and the amount of the movement of the insertion section 2 relative to the wall 106 of lumen toward the proximal direction is also stored in the memory 103. The first movement amount data J1 and the second movement amount data J2 are determined by, for example, the pitch of the spiral fin portion 31, and the angle of inclination of the spiral fin portion 31 relative to the longitudinal axis C.

FIG. 7 is a diagram showing one method of observing the small intestine 105 by the endoscope device 1. When using the endoscope device 1 to observe the small intestine 105, a surgeon needs to recognize the position in the small intestine 105 corresponding to an image to be generated. However, in the small intestine 105, the lumen hardly changes in sectional area, and the folds 107 hardly change in size and shape. That is, in the small intestine 105, characteristics of the lumen and the wall 106 of lumen hardly change. Thus, from the image of the subject alone, it is difficult for the surgeon to recognize the position in the small intestine 105 corresponding to an image to be generated. In the endoscope device (insertion device) 1, when the spiral fin portion 31 is rotating in one of the directions around the longitudinal axis, the wall 106 of lumen moves toward a direction opposite to the movement direction of the insertion section 2. Thus, when the position of the insertion section 2 in the small intestine 105 is detected in accordance with the dimension of the part of the insertion section 2 inserted into the lumen along the longitudinal axis, the detected position of the insertion section 2 may not be proper. Therefore, the surgeon detects the position of the insertion section 2 in the small intestine 105 as will be described later.

As shown in FIG. 7, when the endoscope device 1 is used to observe the small intestine 105, the insertion section 2 is first inserted into the lumen from a mouth (step S151). The distal portion of the insertion section 2 is inserted into the small intestine 105, and the motor 75 is rotationally driven toward the first driving direction. Thus, the rotation unit 30 rotates toward the first around-axis direction (step S152). The insertion section 2 is then inserted by the first propulsive force F1 until the distal end of the insertion section 2 is located at an ileocecal valve 108 between the small intestine 105 and a large intestine 109 (step S153).

Figure 8A:
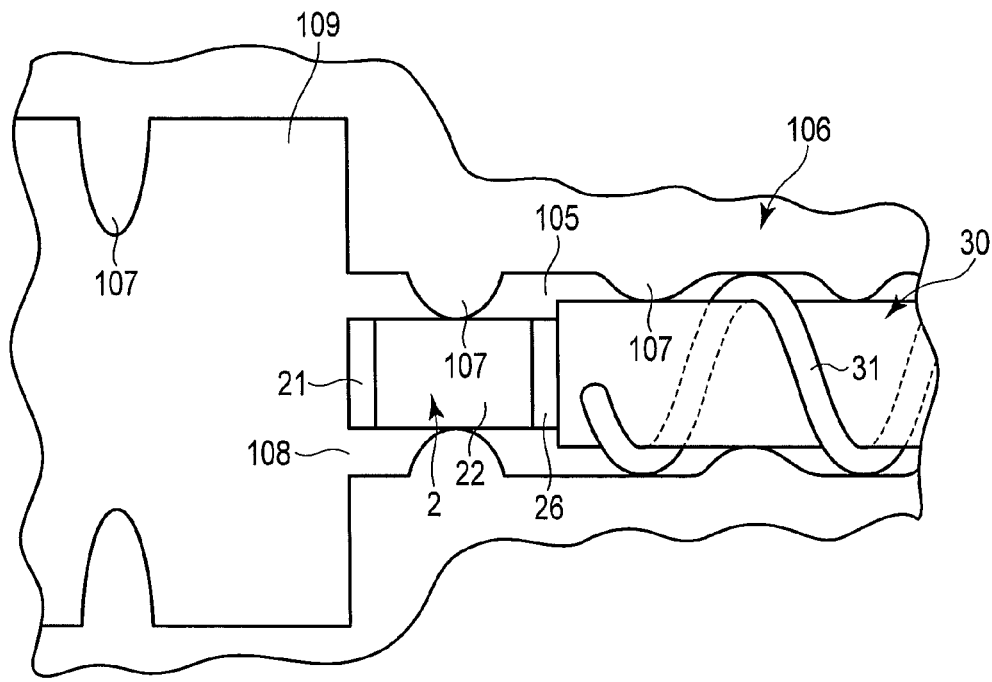
FIG. 8A is a schematic diagram showing a state in which a distal end of the insertion section according to the first embodiment is located in an ileocecal valve between and the small intestine and a large intestine.

FIG. 8A is a diagram showing a state in which the distal end of the insertion section 2 is located in the ileocecal valve 108 between the small intestine 105 and the large intestine 109. As shown in FIG. 8A, since the ileocecal valve 108 is located between the small intestine 105 having a small sectional area and the large intestine 109 having a large sectional area, the sectional area of the lumen rapidly changes in the ileocecal valve 108. The folds 107 vary in shape and size between the small intestine 105 and the large intestine 109, and characteristics of the wall 106 of lumen change. Therefore, from the image of the subject generated by the image processor 11, the surgeon can easily recognize that the distal end of the insertion section 2 is located at the ileocecal valve 108. The surgeon then inputs a position determination operation by use of the position determination operation section 95. As a result, the reference position determiner 101 determines that the position of the insertion section 2 when the distal end of the insertion section 2 is located in the ileocecal valve 108 is a reference position of the insertion section 2. That is, the reference position of the insertion section 2 is determined by the input of the position determination operation (step S154).

The rotation unit 30 is then rotated in one of the directions around the longitudinal axis to move the insertion section 2 in the small intestine 105 along the longitudinal axis C. That is, in the small intestine 105, the insertion section 2 is moved in one of the directions parallel to the longitudinal axis C by the first propulsive force F1 or the second propulsive force F2 (step S155). For example, the rotation unit 30 is rotated toward the second around-axis direction while the insertion section 2 is located at the reference position, so that the insertion section 2 is moved from the reference position toward the proximal direction by the second propulsive force F2. Moreover, the rotation unit 30 is rotated toward the first around-axis direction when the insertion section 2 has moved from the reference position toward the proximal direction by the second propulsive force F2. As a result, the insertion section 2 is moved toward the distal direction by the first propulsive force F1 from the position to which the insertion section 2 has moved by the second propulsive force F2.

Figure 8B:
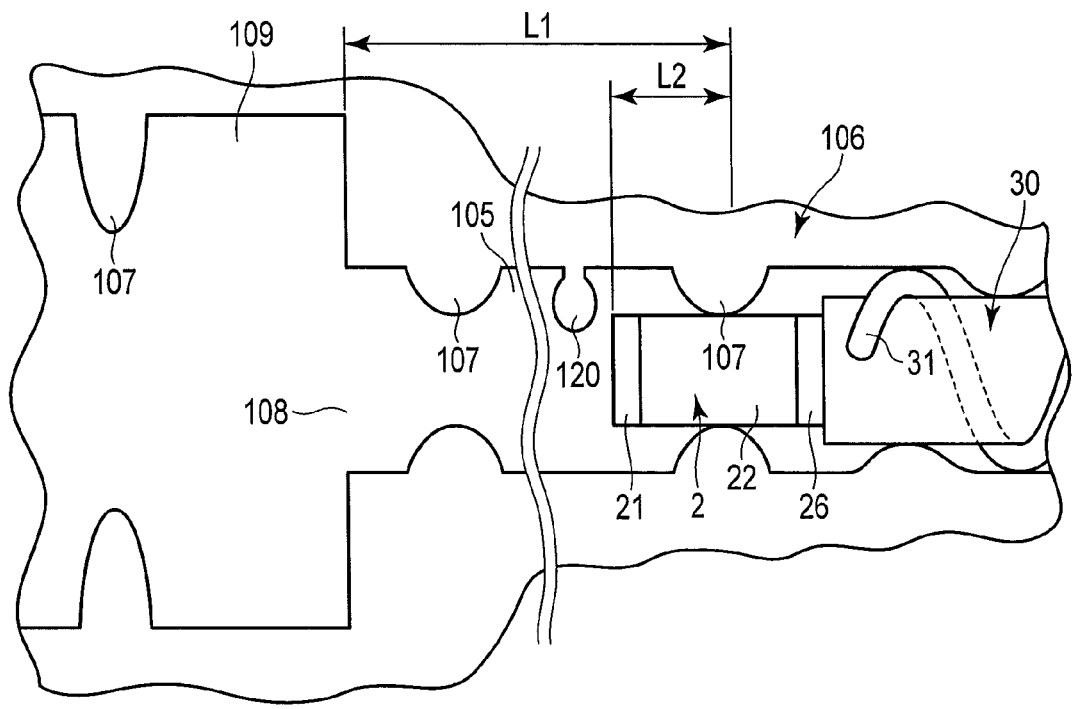
FIG. 8B is a schematic diagram showing a state in which the insertion section according to the first embodiment has moved in the small intestine along a longitudinal axis from a reference position shown in FIG. 8A by a first propulsive force and a second propulsive force.

FIG. 8B is a diagram showing a state in which the insertion section 2 has moved in the small intestine 105 along the longitudinal axis C from the reference position by the first propulsive force F1 and the second propulsive force F2. For example, the insertion section 2 is moved in a movement amount L1 from the reference position toward the proximal direction by the second propulsive force F2, and the insertion section 2 is then moved in a movement amount L2 toward the distal direction by the first propulsive force F1, so that the insertion section 2 is located at a position shown in FIG. 8B. In this case, the distal end of the insertion section 2 is located in the vicinity of an affected part 120 in the small intestine 105. While the distal end of the insertion section 2 is located in the vicinity of the affected area 120, the subject (affected part 120) is imaged by the image pickup element 45 (step S156). That is, the subject is imaged at an after-movement position moved from the reference position. When the insertion section 2 has moved from the reference position along the longitudinal axis C in the small intestine 105, the driving amount and driving direction (driving condition) of the motor 75 are calculated by the driving condition calculator 93 (step S157).

The rotation direction and the rotation amount (rotation condition) of the rotation unit 30 are calculated by the movement displacement calculator 102 in accordance with the calculated driving direction and driving amount of the motor 75 (step S158). Here, when the rotation unit 30 is rotated toward the first around-axis direction, the rotation amount of the rotation unit 30 toward the first around-axis direction is calculated in accordance with the first rotation amount data I1 stored in the memory 103. When the rotation unit 30 is rotated toward the second around-axis direction, the rotation amount of the rotation unit 30 toward the second around-axis direction is calculated in accordance with the second rotation amount data I2 stored in the storage 103.

The movement direction and movement amount of the insertion section 2 (and the rotation unit 30) are calculated by the movement displacement calculator 102 in accordance with the calculated rotation direction and rotation amount of the rotation unit 30 (step S159). As described above, in response to the rotation of the rotation unit 30 toward the first around-axis direction, the insertion section 2 is moved toward the distal direction by the first propulsive force F1 in the small intestine 105. In this case, the movement amount of the insertion section 2 toward the distal direction is calculated in accordance with the first movement amount data J1 stored in the memory 103. In response to the rotation of the rotation unit 30 toward the second around-axis direction, the insertion section 2 is moved toward the proximal direction by the second propulsive force F2 in the small intestine 105. In this case, the movement amount of the insertion section 2 toward the proximal direction is calculated in accordance with the second movement amount data J2 stored in the memory 103.

A movement displacement of the insertion section 2 from the reference position (position indicated in FIG. 8A) in directions parallel to the longitudinal axis C is calculated by the movement displacement calculator 102 in accordance with the movement amount by the first propulsive force F1 and the movement amount by the second propulsive force F2 that have been calculated (step S160). For example, in the condition shown in FIG. 8B, the movement displacement of the insertion section 2 from the reference position is (L1-L2). That is, the insertion section 2 has been displaced (L1-L2) from the reference position in the proximal direction.

As described above, in the condition shown in FIG. 8B, the subject (affected part 120) is imaged (step S153). The imaged subject figure is stored in the memory 103 in association with the movement displacement (L1-L2) of the position where the subject has been imaged with respect to the reference position (step S161). Thus, the imaged subject figure is stored as the subject (affected area 120) at the position where the movement displacement from the reference position is (L1-L2). That is, when the subject is imaged at the after-movement position moved from the reference position, the subject figure at the after-movement position is stored in association with the movement displacement of the after-movement position relative to the reference position. Data regarding the subject figure is stored as described above, so that the position of the imaged subject (affected part 120) in the small intestine 105 can be recognized in accordance with the data regarding the subject figure.

The calculated movement displacement of the insertion section 2 is displayed on the display 13 via the image processor 11 (step S162). Thus, in accordance with the movement displacement from the reference position (ileocecal valve 108), the surgeon can recognize the position in the small intestine 105 corresponding to an image to be generated. When the observation of the small intestine 105 is continued (step S163—No), steps S155 to S162 are performed with time. When the observation of the small intestine 105 is finished (step S163—Yes), the insertion section 2 inserted from the mouth is removed from the lumen (step S164).

Although the position of the insertion section 2 situated when the distal end of the insertion section 2 is located at the ileocecal valve 108 between the small intestine 105 and the large intestine 109 is the reference position in the above explanation, this is not a restriction. For example, when the insertion section 2 is inserted from an anus, the position of the insertion section 2 situated when the distal end of the insertion section 2 is located at the boundary between a duodenum and the small intestine may be the reference position of the insertion section 2. At the boundary between the small intestine and the duodenum, the lumen gradually increases in sectional area from the small intestine to the duodenum. Characteristics of the wall of lumen vary between the small intestine and the duodenum. Thus, from the image of the subject generated by the image processor 11, the surgeon can easily recognize that the distal end of the insertion section 2 is located at the boundary between the small intestine and the duodenum.

Figure 9A:
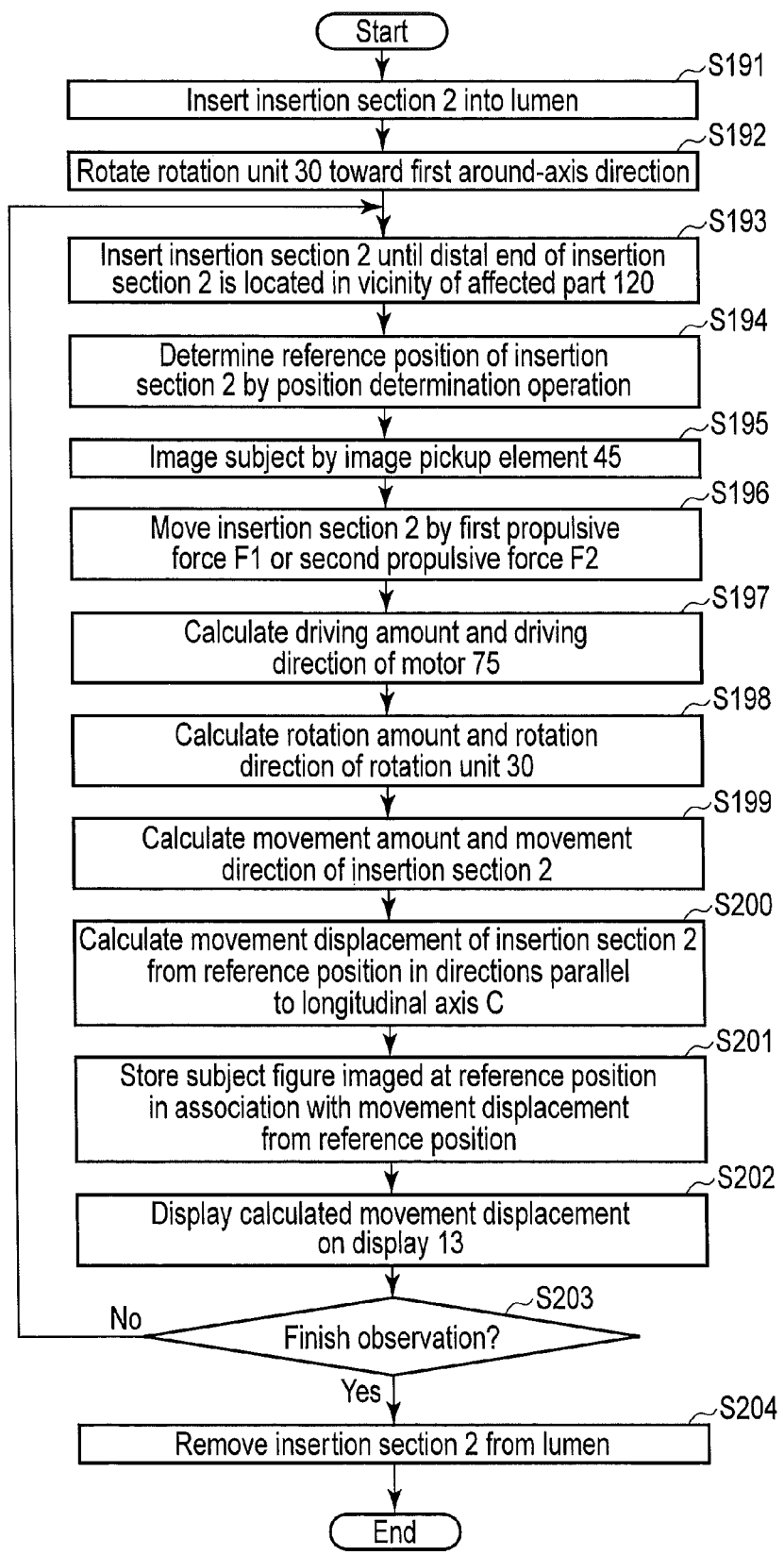
FIG. 9A is a flowchart showing one method different from the method in FIG. 7 of observing the small intestine by the endoscope device according to the first embodiment.

FIG. 9A is a diagram showing another method of observing the small intestine 105 by the endoscope device 1. As shown in FIG. 9A, when the endoscope device 1 is used to observe the small intestine 105, the insertion section 2 is first inserted into the lumen from the anus (step S191).

The distal portion of the insertion section 2 is then inserted into the small intestine 105, and the motor 75 is rotationally driven toward the first driving direction. Thus, the rotation unit 30 rotates toward the first around-axis direction (step S192). The insertion section 2 is then inserted by the first propulsive force F1 until the distal end of the insertion section 2 is located in the vicinity of the affected part 120 in the small intestine 105 (step S193).

Figure 9B:
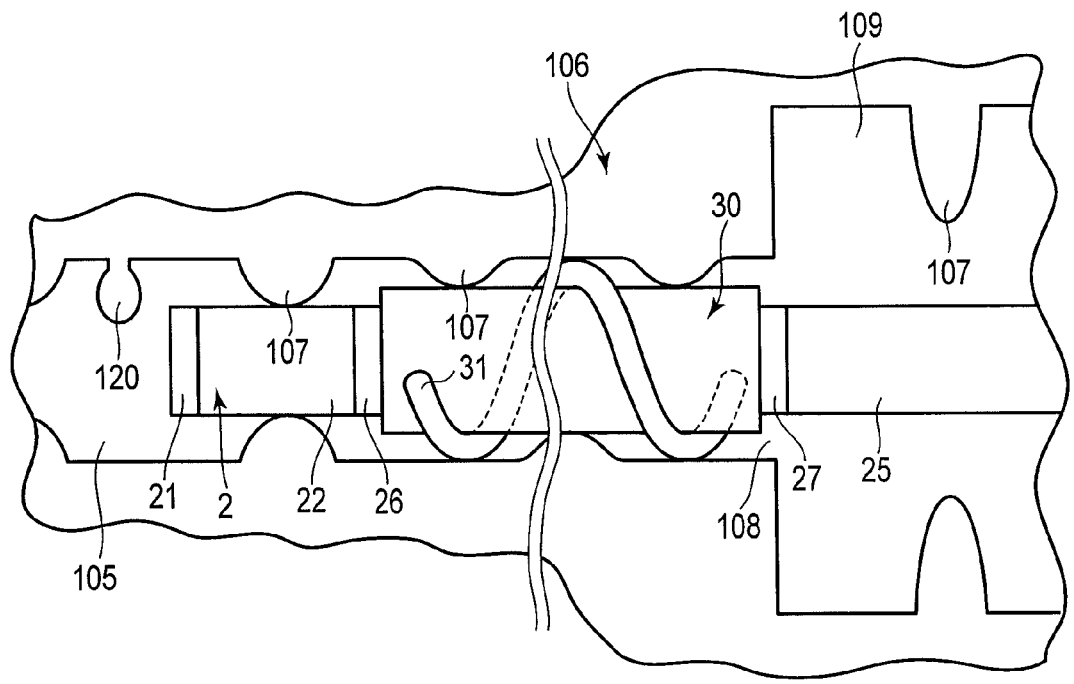
FIG. 9B is a schematic diagram showing a state in which the distal end of the insertion section according to the first embodiment is located in the vicinity of an affected area in the small intestine.

FIG. 9B is a schematic diagram showing a state in which the distal end of the insertion section 2 is located in the vicinity of the affected part 120 of the small intestine 105. As shown in FIG. 9B, the distal end of the insertion section 2 is inserted up to the vicinity of the affected area 120 through the ileocecal valve 108. The surgeon inputs a position determination operation by use of the position determination operation section 95 in a state that the distal end of the insertion section 2 is located in the vicinity of the affected part 120. As a result, the reference position determiner 101 determines that the position of the insertion section 2 situated when the distal end of the insertion section 2 is located in the vicinity of the affected area 120 is the reference position of the insertion section 2. That is, the reference position of the insertion section 2 is determined by the input of the position determination operation (step S194). The subject (affected area 120) is imaged by the image pickup element 45 while the distal end of the insertion section 2 is located in the vicinity of the affected part 120 (step S195). That is, the subject is imaged at the reference position.

The rotation unit 30 is then rotated in one of the directions around the longitudinal axis to move the insertion section 2 in the small intestine 105 along the longitudinal axis C. That is, in the small intestine 105, the insertion section 2 is moved in one of the directions parallel to the longitudinal axis C by the first propulsive force F1 or the second propulsive force F2 (step S196).

Figure 9C:
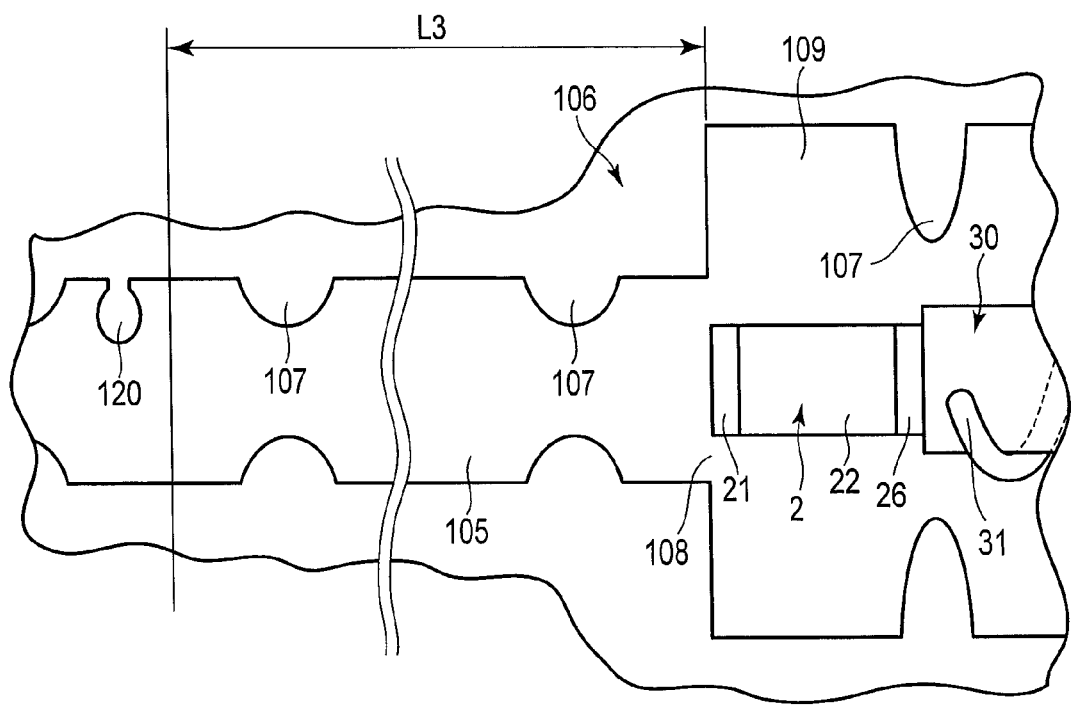
FIG. 9C is a schematic diagram showing a state in which the insertion section according to the first embodiment has moved in the small intestine along the longitudinal axis from the reference position shown in FIG. 9B by the first propulsive force and the second propulsive force.

FIG. 9C is a diagram showing a state in which the insertion section 2 has moved along the longitudinal axis C from the reference position by the first propulsive force F1 and the second propulsive force F2. For example, the insertion section 2 is moved in a movement amount L3 from the reference position toward the proximal direction by the second propulsive force F2, so that the insertion section 2 is located at a position shown in FIG. 9C. In this case, the distal end of the insertion section 2 is located in the ileocecal valve 108 between the small intestine 105 and the large intestine 109. That is, the insertion section 2 is located at the after-movement position moved from the reference position. When the insertion section 2 has moved from the reference position along the longitudinal axis C in the small intestine 105, the driving amount and driving direction (driving condition) of the motor 75 are calculated by the driving condition calculator 93 (step S197).

The rotation direction and the rotation amount (rotation condition) of the rotation unit 30 are calculated by the movement displacement calculator 102 in accordance with the calculated driving direction and driving amount of the motor 75 (step S198). The movement direction and movement amount of the insertion section 2 (and the rotation unit 30) are then calculated by the movement displacement calculator 102 in accordance with the calculated rotation direction and rotation amount of the rotation unit 30 (step S199). At the same time, the movement amount of the insertion section 2 is calculated in accordance with the first movement amount data J1 and the second movement amount data J2 as described above.

A movement displacement of the insertion section 2 from the reference position (position indicated in FIG. 9B) in the directions parallel to the longitudinal axis C is calculated by the movement displacement calculator 102 in accordance with the movement amount by the first propulsive force F1 and the movement amount by the second propulsive force F2 that have been calculated (step S200). For example, in the condition shown in FIG. 9C, the movement displacement of the insertion section 2 from the reference position is L3. That is, the insertion section 2 has been displaced L3 from the reference position in the proximal direction.

As described above, at the reference position (in the condition shown in FIG. 9B), the subject (affected part 120) is imaged (step S195). The imaged subject figure is stored in the memory 103 in association with the movement displacement (L3) of the after-movement position where the distal end of the insertion section 2 is located in the ileocecal valve 108 with respect to the reference position (step S201). Thus, the imaged subject figure is stored as the subject (affected area 120) at the reference position where the movement displacement when the distal end of the insertion section 2 is located in the ileocecal valve 108 is L3. That is, when the subject is imaged at the reference position, the subject figure at the reference position is stored in association with the movement displacement of the after-movement position moved from the reference position relative to the reference position. Data regarding the subject figure is stored as described above, so that the position of the imaged subject (affected part 120) in the small intestine 105 can be recognized in accordance with the data regarding the subject figure. As described above, from the image of the subject generated by the image processor 11, the surgeon can easily recognize that the distal end of the insertion section 2 is located at the ileocecal valve 108.

The calculated movement displacement of the insertion section 2 is displayed on the display 13 via the image processor 11 (step S202). When the observation of the small intestine 105 is continued (step S203—No), steps S193 to S202 are performed with time. When the observation of the small intestine 105 is finished (step S203—Yes), the insertion section 2 inserted from the anus is removed from the lumen (step S204).

In the endoscope device 1 described above, the rotation direction and the rotation amount of the rotation unit 30 are calculated in accordance with the driving direction and driving amount of the motor 75 which is the driving member. The movement displacement of the insertion section 2 from the reference position in the directions parallel to the longitudinal axis C is calculated in accordance with the calculated rotation direction and rotation amount of the rotation unit. Therefore, for example, if the position of the insertion section 2 situated when the distal end of the insertion section 2 is located in the ileocecal valve 108 is input as the reference position, the position of the insertion section 2 can be properly detected in the small intestine 105. As a result, the surgeon can properly recognize the position in the small intestine 105 corresponding to an image to be generated.

Since the movement displacement of the insertion section 2 from the reference position is calculated in accordance with the rotation direction and the rotation amount of the rotation unit, a calculation is performed in consideration of the movement of the wall 106 of lumen toward the proximal direction by the reaction force Pa1 against the first propulsive force F1 and the movement of the wall 106 of lumen toward the distal direction by the reaction force Pa2 against the propulsive force P2. Thus, the position of the insertion section 2 can be more properly detected in the small intestine 105.

Second Embodiment

Now, a second embodiment of the present invention is described with reference to FIG. 10 to FIG. 13. In the second embodiment, the configuration according to the first embodiment is modified as below. The same parts as those in the first embodiment are provided with the same reference numerals, and are not described.

FIG. 10 is a diagram showing the configuration of the control unit 15 according to the present embodiment. According to the present embodiment, the control unit 15 includes the drive current supplier 91, the drive controller 92, the driving condition calculator 93, the movement displacement calculator 102, and the memory 103, as in the first embodiment. According to the present embodiment, the control unit 15 is provided with an idle state detector 111.

The idle state detector 111 is electrically connected to the drive controller 92, the movement displacement calculator 102, and the memory 103.

FIG. 11 is a diagram showing a method of observing the small intestine 105 by the endoscope device 1. As shown in FIG. 11, according to the present embodiment, steps S151 to S157 are performed in the observation of the small intestine 105, as in the method shown in FIG. 7 according to the first embodiment. Here, when the insertion section 2 moves in the small intestine 105 in one of the directions parallel to the longitudinal axis C in response to the rotation of the rotation unit 30 in one of the directions around the longitudinal axis, the first propulsive force F1 or the second propulsive force F2 may not be generated due to, for example, body fluid. That is, even when the rotation unit 30 rotates in one of the direction around the longitudinal axis, the idle state may occur so that the first propulsive force F1 and the second propulsive force F2 are not applied to the insertion section 2 and the rotation unit 30.

According to the present embodiment, the idle state detector 111 detects the idle state after the driving direction and driving amount of the motor 75 are calculated in step S157. That is, whether the idle state has occurred is judged (step S165). When the idle state has not occurred (step S165—No), steps S158 to S159 are performed as in the first embodiment, and the movement displacement of the insertion section 2 from the reference position in the directions parallel to the longitudinal axis C is calculated in step S160.

On the other hand, when the idle state has occurred (step S165—Yes), the movement displacement calculator 102 calculates that the movement amount of the insertion section 2 in the directions parallel to the longitudinal axis C is zero (step S166). That is, it is judged that the insertion section 2 does not move along the longitudinal axis C in the idle state. The movement displacement of the insertion section 2 from the reference position is calculated in step S160 in accordance with the calculated movement amount (i.e., zero) of the insertion section 2 in the idle state.

The imaged subject figure is stored in association with the movement displacement of the insertion section 2 from the reference position calculated in step S160 (step S161). The calculated movement displacement of the insertion section 2 from the reference position is displayed on the display 13 (step S162). When the observation of the small intestine 105 is continued (step S163—No), steps S155 to S157, S165, and S158 to S162, or steps S155 to S157, S165, S166, and S160 to S162 are performed with time.

Figure 12:
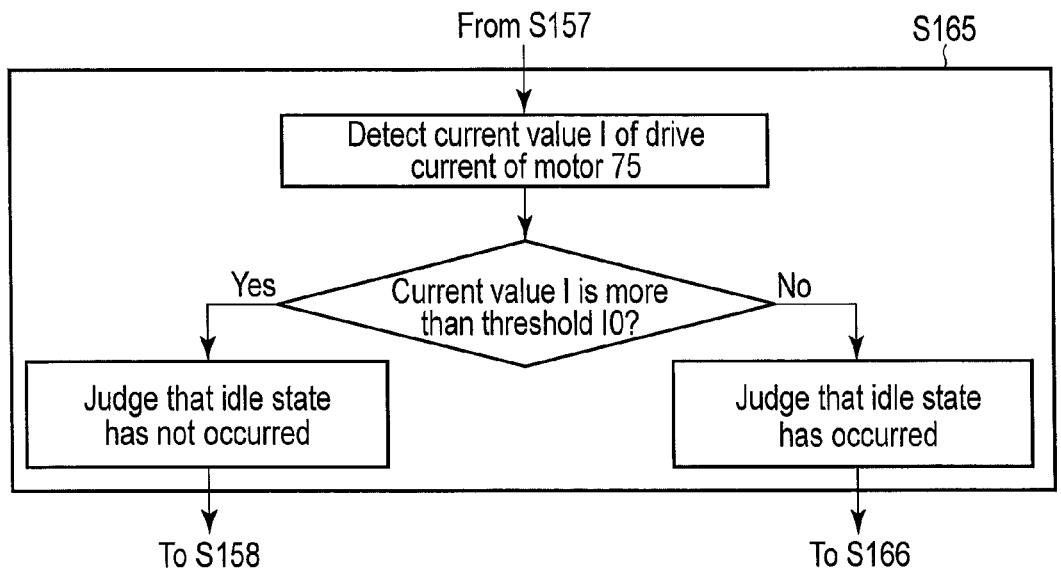
FIG. 12 is a flowchart showing a method of detecting an idle state by an idle state detector of the control unit according to the second embodiment.

FIG. 12 is a diagram showing a method of detecting the idle state. As shown in FIG. 12, in order to detect the idle state, the drive controller 92 first detects a current value I of the drive current of the motor 75 (step S171). The idle state detector 111 then judges whether the detected current value I is more than a threshold I0 (step S172). In the idle state, a press force applied to the spiral fin portion 31 from the wall 106 of lumen is lower. Thus, in the idle state, the driving force to rotate the rotation unit 30 is lower, and the current value I of the drive current supplied to the motor 75 is lower.

When the current value I of the drive current is more than the threshold I0 (step S172—Yes), the idle state detector 111 judges that the idle state has not occurred (step S173). On the other hand, when the current value I of the drive current is equal to or less than the threshold I0 (step S172—No), the idle state detector 111 judges that the idle state has occurred (step S174).

Figure 13:
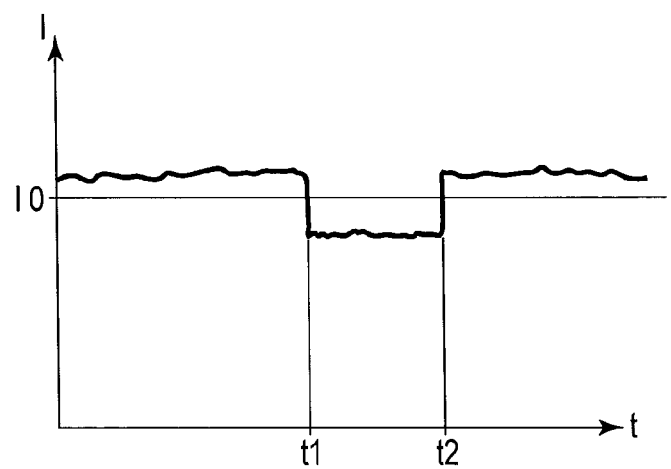
FIG. 13 is a schematic diagram showing an example of a change of a drive current supplied to a motor according to the second embodiment with time.

FIG. 13 is a diagram showing an example of a change of the drive current supplied to the motor 75 with time. In the example shown in FIG. 13, the current value I of the drive current is less than the threshold I0 between a time t1 and a time t2. Therefore, the idle state detector 111 judges that the idle state has occurred between the time t1 and the time t2. In this way, the idle state is detected in accordance with the change of the drive current supplied to the motor 75 with time. Here, the threshold I0 of the current value I of the drive current is stored in the memory 103.

As described above, in the endoscope device 1 according to the present embodiment, the idle state is detected by the idle state detector 111. When the idle state has occurred, the movement displacement calculator 102 calculates that the movement amount of the insertion section 2 in the directions parallel to the longitudinal axis C is zero. The movement displacement of the insertion section 2 from the reference position is calculated in accordance with the calculated movement amount (i.e., zero) of the insertion section 2 in the idle state. Thus, the position of the insertion section 2 can be more properly detected in the small intestine 105.

Modification of Second Embodiment

Figure 14:
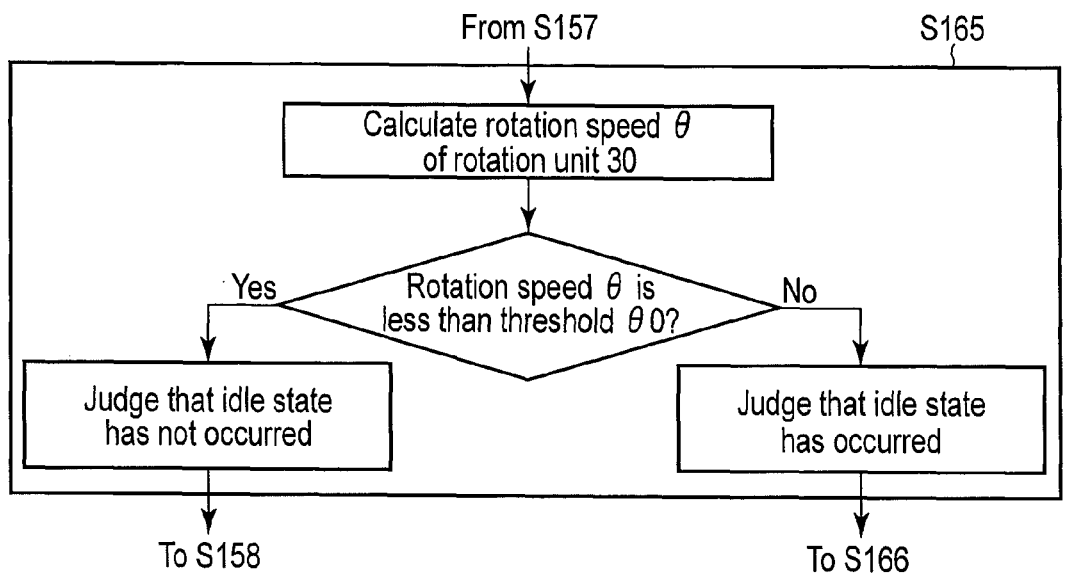
FIG. 14 is a flowchart showing a method of detecting the idle state by the idle state detector of the control unit according to a modification of the second embodiment.

Although the idle state is detected in accordance with the change of the drive current with time according to the second embodiment, this is not a restriction. For example, as in a modification shown in FIG. 14 and FIG. 15, the idle state detector 111 may detect the idle state based on the change of the rotation speed of the rotation unit 30 with time.

According to the present modification, the idle state detector 111 calculates a rotation speed θ of the rotation unit 30 from the rotation amount of the rotation unit 30 calculated by the movement displacement calculator 102 (step S175). At the same time, the rotational acceleration of the rotation unit 30 may be calculated. The idle state detector 111 then judges whether the calculated rotation speed θ is less than a threshold θ0 (step S176). In the idle state, a press force applied to the spiral fin portion 31 from the wall of lumen 106 is lower. Thus, in the idle state, the rotation speed θ of the rotation unit 30 is higher.

When the rotation speed θ is less than the threshold θ0 (step S176—Yes), the idle state detector 111 judges that the idle state has not occurred (step S177). On the other hand, when the rotation speed θ is equal to or more than the threshold θ0 (step S176—No), the idle state detector 111 judges that the idle state has occurred (step S178).

Figure 15:
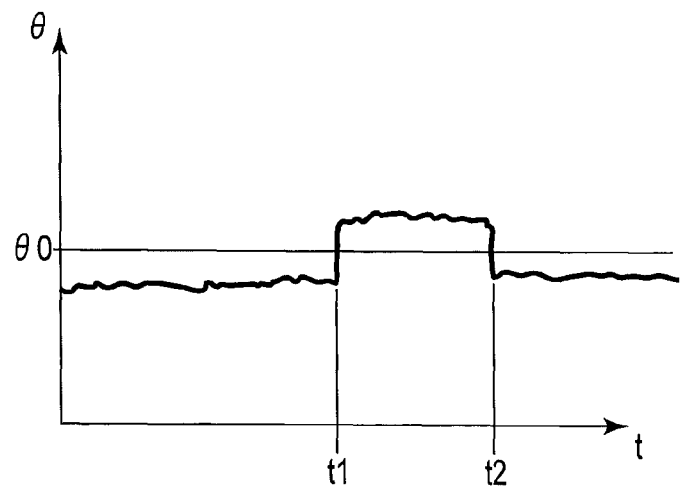
FIG. 15 is a schematic diagram showing an example of a change of the rotation speed of the rotation unit according to the modification of the second embodiment with time.

In the example shown in FIG. 15, the rotation speed θ of the rotation unit 30 is equal to or more than the threshold θ0 between the time t1 and the time t2. Therefore, the idle state detector 111 judges that the idle state has occurred between the time t1 and the time t2. In this way, the idle state is detected in accordance with the change of the rotation speed of the rotation unit 30 with time. Here, the threshold θ0 of the rotation speed θ is stored in the memory 103.

The idle state may be detected in accordance with the change of the rotational acceleration with time instead of the rotation speed θ. As in the case of the rotation speed, the rotational acceleration of the rotation unit 30 is higher in the idle state.

Third Embodiment

Now, a third embodiment of the present invention is described with reference to FIG. 16 and FIG. 17. In the third embodiment, the configuration according to the first embodiment is modified as below. The same parts as those in the first embodiment are provided with the same reference numerals, and are not described.

Figure 16:
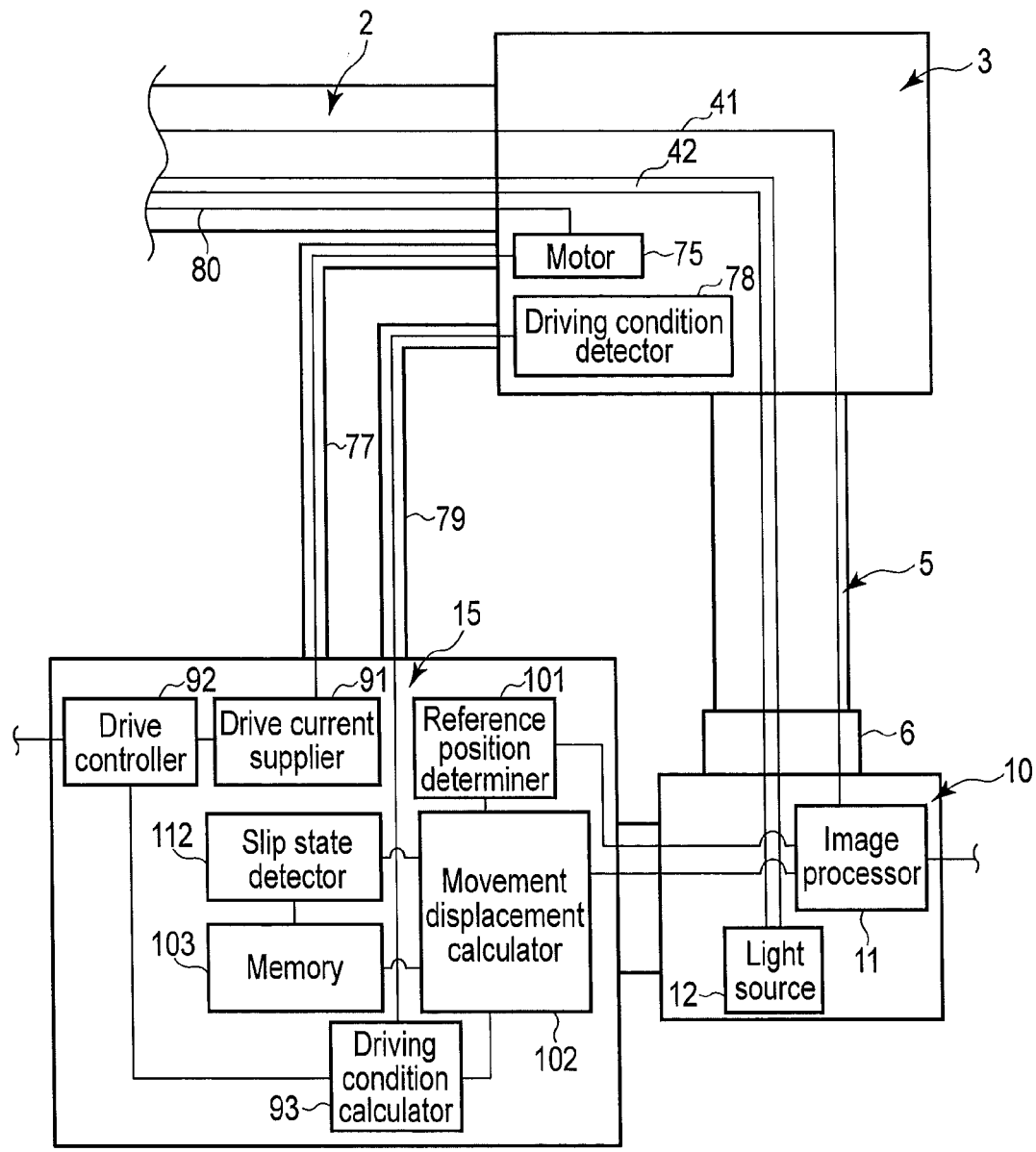
FIG. 16 is a schematic block diagram showing the configurations of an operation section, an observation processing unit, and a control unit of an endoscope device according to a third embodiment.

FIG. 16 is a schematic block diagram showing the configurations of the operation section 3, the observation processing unit 10, and the control unit 15 according to the present embodiment. According to the present embodiment, the control unit 15 includes the drive current supplier 91, the drive controller 92, the driving condition calculator 93, the movement displacement calculator 102, and the memory 103, as in the first embodiment. According to the present embodiment, the reference position determiner 101 is electrically connected to the image processor 11. According to the present embodiment, the position determination operation section 95 is not provided. A slip state detector 112 is provided in the control unit 15. The slip state detector 112 is electrically connected to the movement displacement calculator 102 and the memory 103.

Figure 17:
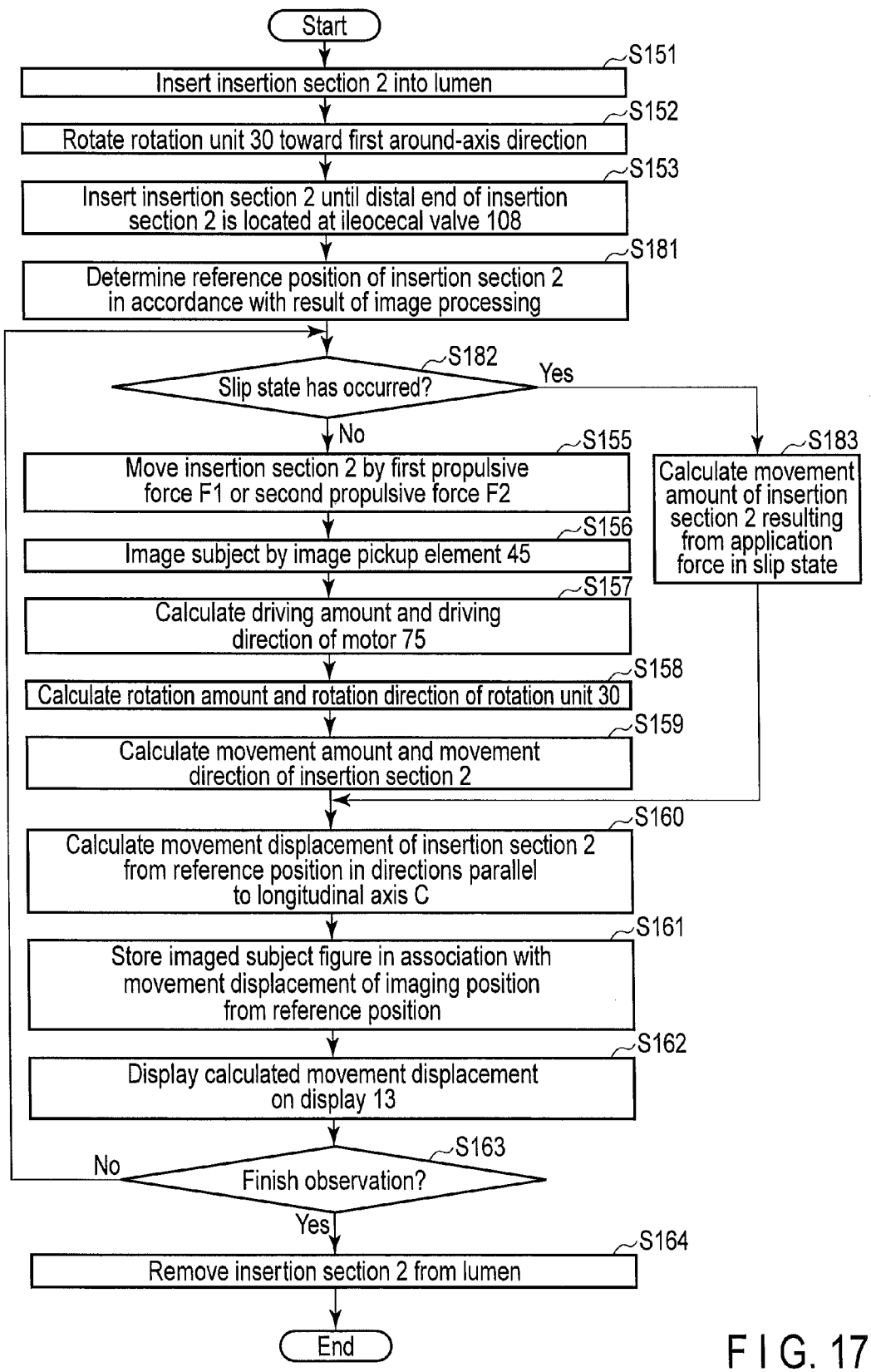
FIG. 17 is a flowchart showing a method of observing the small intestine by the endoscope device according to the third embodiment.

FIG. 17 is a diagram showing a method of observing the small intestine 105 by the endoscope device 1. As shown in FIG. 17, according to the present embodiment, steps S151 to S153 are performed in the observation of the small intestine 105, as in the method shown in FIG. 7 according to the first embodiment.

According to the present embodiment, the position determination operation is not performed because the position determination operation section 95 is not provided. Instead, the reference position determiner 101 determines the reference position of the insertion section 2 in accordance with the result of the image processing in the image processor 11 (step S181). As described above, the sectional area of the lumen rapidly changes in the ileocecal valve 108, and the folds 107 vary in shape and size between the small intestine 105 and the large intestine 109. Therefore, from the result of the image processing in the image processor 11, the reference position determiner 101 can easily detect that the distal end of the insertion section 2 is located at the ileocecal valve 108. The condition in which the distal end of the insertion section 2 is located in the ileocecal valve 108 is detected, and the position of the insertion section 2 in the detected condition is determined as the reference position.

Here, in the observation of the small intestine 105 by the endoscope device 1, the insertion section 2 may move toward one of the directions parallel to the longitudinal axis C due to, for example, body fluid even if the rotation unit 30 does not rotate in one of the directions around the longitudinal axis. That is, a slip state may occur so that the insertion section 2 moves in one of the directions parallel to the longitudinal axis C in response to an application force different from the first propulsive force F1 and the second propulsive force F2.

According to the present embodiment, the slip state is detected by the slip state detector 112 before the insertion section 2 is moved along the longitudinal axis C by the first propulsive force F1 or the second propulsive force F2 due to the rotation of the rotation unit in one of the directions around the longitudinal axis in step S155. That is, whether the slip state has occurred is judged (step S182). The occurrence of the slip state is judged by the change of the image of the subject generated by the image processor 11 with time. For example, the size and shape of a dark part of the lumen change in the image of the subject in response to the movement of the insertion section 2 along the longitudinal axis C in the slip state.

When the slip state has not occurred (step S182—No), steps S155 to S159 are performed as in the first embodiment, and the movement displacement of the insertion section 2 from the reference position in the directions parallel to the longitudinal axis C is calculated in step S160.

On the other hand, when the slip state has occurred (step S182—Yes), the movement displacement calculator 102 calculates the movement amount of the insertion section 2 in one of the directions parallel to the longitudinal axis resulting from the application force in the slip state (step S183). In accordance with the calculated movement amount in the slip state, the movement displacement of the insertion section 2 from the reference position in the directions parallel to the longitudinal axis C is then calculated in step S160. Here, the movement amount of the insertion section 2 resulting from the application force in the slip state is calculated based on the change of the image of the subject generated by the image processor 11 with time. The movement amount of the insertion section 2 in one of the directions parallel to the longitudinal axis C resulting from the application force in the slip state is calculated in accordance with the change in the size and shape of a dark part of the lumen in the image of the subject with time.

The imaged subject figure is stored in association with the movement displacement of the insertion section 2 from the reference position calculated in step S160 (step S161). The calculated movement displacement of the insertion section 2 from the reference position is displayed on the display 13 (step S162). When the observation of the small intestine 105 is continued (step S163—No), steps S182, and S155 to S162, or steps S182, S183, and S160 to S162 are performed with time.

As described above, in the endoscope device 1 according to the present embodiment, the slip state is detected by the slip state detector 112. When the slip state has occurred, the movement displacement calculator 102 calculates the movement amount of the insertion section 2 toward one of the directions parallel to the longitudinal axis C resulting from the application force in the slip state. The movement displacement of the insertion section 2 from the reference position is calculated in accordance with the calculated movement amount of the insertion section 2 in the slip state. Thus, the position of the insertion section 2 can be more properly detected in the small intestine 105.

Other Modifications

According to the embodiments described above, the endoscope device (1) has only to include the spiral fin portion 31 spirally extending along the longitudinal axis C, and to be provided with the rotation unit 30 rotatable relative to the insertion section 2 in the directions around the longitudinal axis. The first propulsive force F1 toward the distal direction has only to be then applied to the insertion section 2 and the rotation unit 30 by the rotation of the rotation unit 30 toward the first around-axis direction in the all-roundly pressed condition in which a press force is applied all-roundly in the directions around the longitudinal axis to the spiral fin portion 31 toward the inner peripheral direction. Moreover, the second propulsive force F2 toward the proximal direction has only to be applied to the insertion section 2 and the rotation unit 30 by the rotation of the rotation unit 30 toward the second around-axis direction in the all-roundly pressed condition. The reference position of the insertion section 2 has only to be determined by the reference position determiner 101. The movement displacement calculator 102 has only to then calculate the rotation direction and the rotation amount of the rotation unit 30 in accordance with the driving direction and driving amount of the driving member (35), and calculate the movement displacement of the insertion section 2 from the reference position in the directions parallel to the longitudinal axis C in accordance with the rotation direction and the rotation amount of the rotation unit 30.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
an insertion section extending from a proximal side toward a distal side along a longitudinal axis;
a rotation unit provided on an outer peripheral side of the insertion section, and being rotatable relative to the insertion section around the longitudinal axis, the rotation unit including a spiral fin portion spirally extending around the longitudinal axis;
a driving motor which is configured to be driven to generate a driving force of rotating the rotation unit;
a driving force transmission which is configured to transmit the driving force generated in the driving motor to the rotation unit, the rotation unit being configured to rotate by the transmitted driving force when the fin portion is pressed toward an inner peripheral side so that a propulsive force is applied to the insertion section and the rotation unit toward the distal side or the proximal side; and
a controller configured to:
determine a reference position that is a position of the insertion section serving as a reference;
detect an idle state in which the propulsive force is not applied to the insertion section and the rotation unit when the rotation unit rotates around the longitudinal axis; and
calculate a rotation direction and a rotation amount of the rotation unit in accordance with a driving direction and a driving amount of the driving motor, calculate a movement displacement of the insertion section from the reference position toward the distal side and the proximal side in accordance with the rotation direction and the rotation amount of the rotation unit, and calculate the movement displacement of the insertion section from the reference position so that a movement amount of the insertion section toward the distal side and the proximal side is zero while the idle state is detected.

2. The insertion device according to claim 1, wherein the controller is further configured to detect the idle state in accordance with at least one of a change of a drive current to drive the driving motor with time, a change of a rotation speed of the rotation unit with time, and a change of a rotational acceleration of the rotation unit with time.

3. The insertion device according to claim 2, wherein the driving force transmission is configured to apply the propulsive force toward the distal side to the insertion section and the rotation unit by rotating the rotation unit toward a first around-axis direction, which is one side around the longitudinal axis, when the fin portion is pressed toward the inner peripheral side, and the driving force transmission is configured to apply the propulsive force toward the proximal side to the insertion section and the rotation unit by rotating the rotation unit toward a second around-axis direction, which is opposite to the first around-axis direction, when the fin portion is pressed toward the inner peripheral side.

4. The insertion device according to claim 3, further comprising:
a memory configured to store rotation amount data indicating the relation between the driving amount of the driving motor and the rotation amount of the rotation unit toward the first around-axis direction, and movement amount data indicating the relation between the rotation amount of the rotation unit toward the first around-axis direction and a movement amount of the insertion section toward the distal side,
wherein the controller is further configured to calculate the movement amount of the insertion section toward the distal side resulting from the propulsive force towards the distal side in accordance with the rotation amount data and the movement amount data, and calculate the movement displacement of the insertion section from the reference position in accordance with the calculated movement amount.

5. The insertion device according to claim 3, further comprising:
a memory configured to store rotation amount data indicating the relation between the driving amount of the driving motor and the rotation amount of the rotation unit toward the second around-axis direction, and movement amount data indicating the relation between the rotation amount of the rotation unit toward the second around-axis direction and a movement amount of the insertion section toward the proximal side,
wherein the controller is further configured to calculate the movement amount of the insertion section toward the proximal side resulting from the propulsive force toward the proximal side in accordance with the rotation amount data and the movement amount data, and calculate the movement displacement of the insertion section from the reference position in accordance with the calculated movement amount.

6. The insertion device according to claim 3, wherein the controller is further configured to:
detect a slip state in which the insertion section moves toward the distal side or the proximal side in response to an application force different from the propulsive force generated by the rotation of the rotation unit around the longitudinal axis,
calculate a movement amount of the insertion section towards the distal end or the proximal side resulting from the application force in the slip state, and
calculate the movement displacement of the insertion section from the reference position in accordance with the calculated movement amount.

7. The insertion device according to claim 6, further comprising:
an image pickup element configured to image a subject; and
the controller is further configured to:
perform image processing of an imaged subject figure and to generate an image of the subject,
detect the slip state in accordance with a change of the image generated with time, and
calculate the movement amount of the insertion section resulting from the application force in the slip state in accordance with the change of the image generated with time.

8. The insertion device according to claim 1, further comprising:
a position determination operation switch configured to input a position determination operation of determining the reference position of the insertion section, wherein the controller is further configured to determine the reference position of the insertion section in accordance with the position determination operation in the position determination operation switch.

9. The insertion device according to claim 8, further comprising:
   an image pickup element configured to image a subject; and
   a memory configured to store a subject figure at the reference position in association with the movement displacement of an after-movement position moved from the reference position relative to the reference position when the subject is imaged at the reference position.

10. The insertion device according to claim 8, wherein the controller is further configured to determine, as the reference position, a position of the insertion section situated when an operation signal is transmitted from the position determination operation switch by the position determination operation.

11. The insertion device according to claim 8, further comprising:
    an image pickup element configured to image a subject; and
    a memory configured to store a subject figure at the after-movement position in association with the movement displacement of the after-movement position relative to the reference position when the subject is imaged at the after-movement position to which the insertion section has moved from the reference position.

12. The insertion device according to claim 1, further comprising:
    an image pickup element configured to image a subject; and
    the controller is further configured to:
       perform image processing of an imaged subject figure and configured to generate an image of the subject,
       determine the reference position of the insertion section in accordance with the image processing.

* * * * *